US010542996B2

(12) United States Patent
Willard et al.

(10) Patent No.: US 10,542,996 B2
(45) Date of Patent: Jan. 28, 2020

(54) VESSEL CLOSURE DEVICE

(71) Applicant: Covidien LP, Mansfield, MA (US)

(72) Inventors: Martin Willard, Burnsville, MN (US);
Benjamin Breit, Edina, MN (US);
James Griffin, Evanston, IL (US)

(73) Assignee: Covidien LP, Mansfield, MA (US)

( * ) Notice: Subject to any disclaimer, the term of this patent is extended or adjusted under 35 U.S.C. 154(b) by 220 days.

(21) Appl. No.: 15/634,486

(22) Filed: Jun. 27, 2017

(65) Prior Publication Data
US 2018/0368857 A1  Dec. 27, 2018

(51) Int. Cl.
*A61B 17/08* (2006.01)
*A61B 17/12* (2006.01)

(52) U.S. Cl.
CPC .. *A61B 17/12163* (2013.01); *A61B 17/12009* (2013.01); *A61B 2017/1205* (2013.01)

(58) Field of Classification Search
CPC ......... A61B 17/12; A61B 17/08; A61B 17/10; A61B 17/0057; A61B 17/12163; A61B 17/12009; A61B 2017/1205; A61B 2017/00637; A61B 2017/00654
See application file for complete search history.

(56) References Cited

U.S. PATENT DOCUMENTS

| | | | |
|---|---|---|---|
| RE34,021 E | 8/1992 | Mueller et al. | |
| 5,591,204 A | 1/1997 | Janzen et al. | |
| 5,725,551 A | 3/1998 | Myers et al. | |
| 6,077,279 A | 6/2000 | Kontos | |
| 6,551,303 B1 | 4/2003 | Van Tassel et al. | |
| 6,890,342 B2 | 5/2005 | Zhu et al. | |
| 7,213,601 B2 | 5/2007 | Stevens et al. | |
| 7,303,571 B2 | 12/2007 | Makower et al. | |
| 7,597,705 B2 | 10/2009 | Forsberg et al. | |
| 8,475,492 B2 | 7/2013 | Raabe et al. | |
| 8,632,454 B2 * | 1/2014 | Lashinski | A61B 17/0401 600/37 |
| 8,784,439 B1 | 7/2014 | Ward et al. | |

(Continued)

FOREIGN PATENT DOCUMENTS

| | | |
|---|---|---|
| WO | 2013049682 A1 | 4/2013 |
| WO | 2015144898 A2 | 10/2015 |

OTHER PUBLICATIONS

Extended Search Report from counterpart European Application No. 18176953.0, dated Mar. 20, 2019, 13 pp.

(Continued)

*Primary Examiner* — Vi X Nguyen

(57) ABSTRACT

In some examples, a vessel closure system includes a catheter configured to be introduced into a vessel of a patient, the catheter defining a catheter lumen, and a closure device configured to be received within the catheter lumen. In some instances, the closure device may include an elongated flexible member and one or more anchors attached to the elongated flexible member. The anchors may be distributed along a length of the elongated flexible member, and each anchor may include an anchor head configured to be introduced into a wall of the vessel and engage with the wall of the vessel to cause the wall to move radially inward in response to a proximal pulling force applied to the elongated flexible member.

25 Claims, 14 Drawing Sheets

(56) References Cited

U.S. PATENT DOCUMENTS

| | | | |
|---|---|---|---|
| 2007/0112425 A1* | 5/2007 | Schaller | A61B 17/00234 623/2.37 |
| 2009/0264920 A1 | 10/2009 | Berenstein | |
| 2012/0109191 A1 | 5/2012 | Marano, Jr. et al. | |
| 2012/0277774 A1 | 11/2012 | Guo | |
| 2012/0277782 A1 | 11/2012 | Brandeis | |
| 2014/0336672 A1 | 11/2014 | Walters et al. | |
| 2015/0250522 A1 | 9/2015 | Shimizu et al. | |

OTHER PUBLICATIONS

Search Report from counterpart European Application No. 18176953.0, dated Dec. 6, 2018, 14 pp.

\* cited by examiner

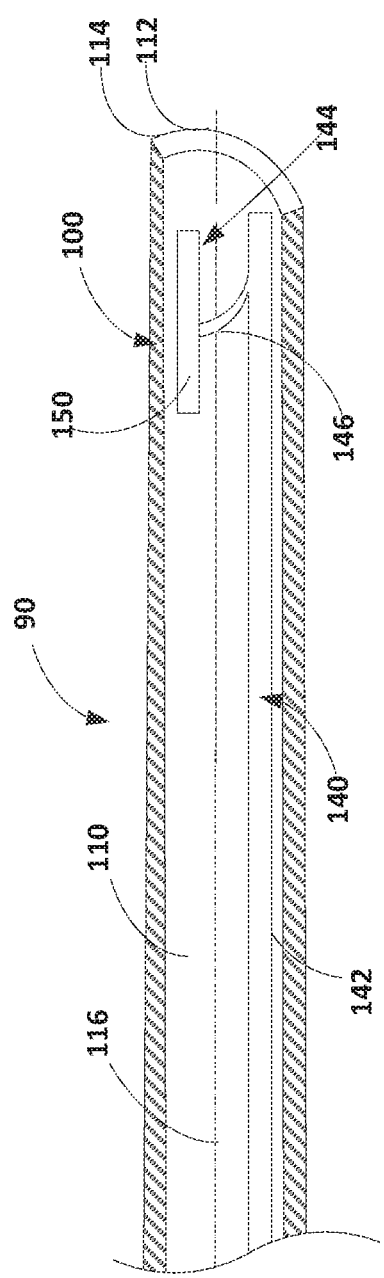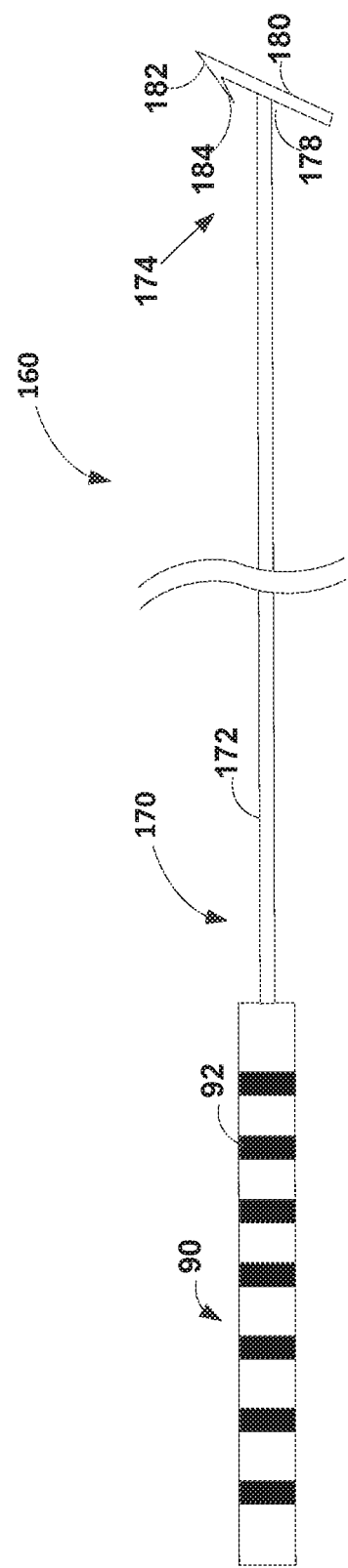

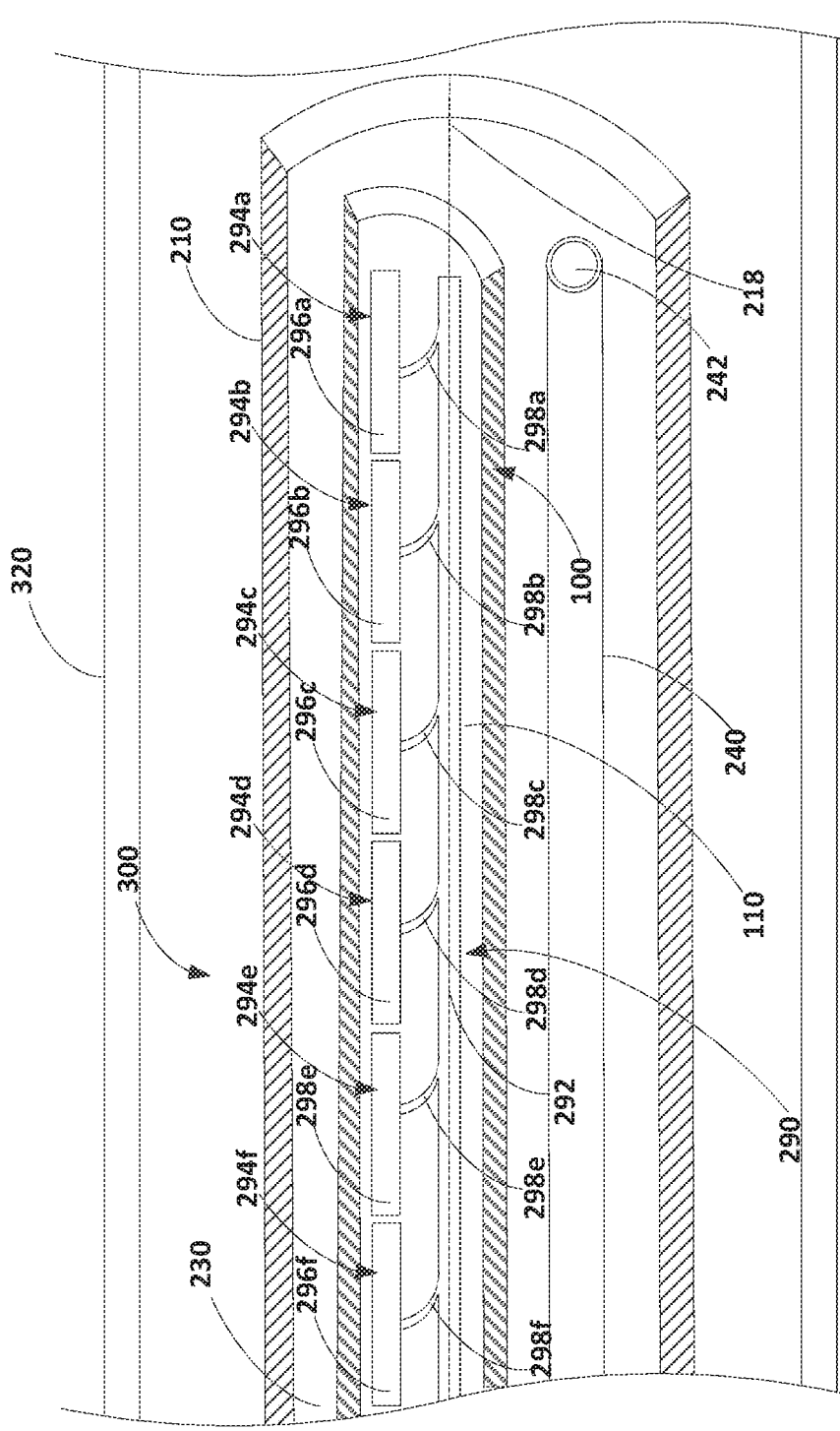

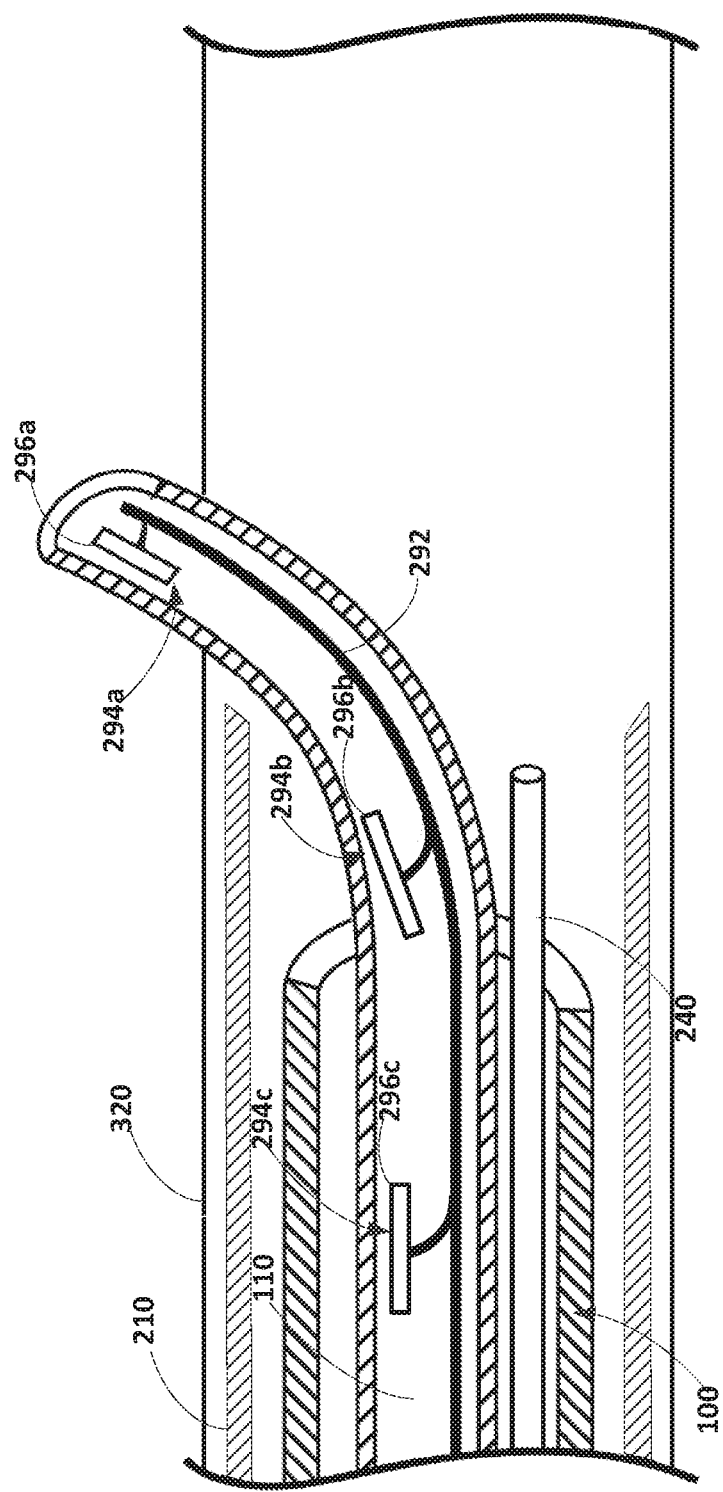

VESSEL CLOSURE DEVICE

TECHNICAL FIELD

The disclosure relates generally to closing and occluding a vessel within the body of a patient, and more specifically to vessel closure devices, vessel closure systems, and methods of using the vessel closure devices and vessel closure systems.

BACKGROUND

Portions of the vasculature of a patient may be treated to prevent blood flow through a target blood vessel. Conditions for which vessel closure may be indicated include tumors, aneurysms, arteriovenous malformations, varicose veins, and others. In some examples, a vessel closure system may include a catheter for delivering an adhesive or a sclerosing agent to a treatment site within a target vessel. During treatment, a clinician may apply external pressure to the treatment site after delivering the adhesive, thereby causing the target vessel to collapse onto the adhesive. Some vessel closure systems may include coils, plugs, or other devices that may be placed within the target vessel to prevent blood flow, instead of or in addition to adhesives or sclerosing agents.

SUMMARY

This disclosure describes example vessel closure devices that can be used, for example, to collapse a target vessel at a treatment site from within the vasculature of a patient. The disclosure also describes example vessel closure systems that may include a catheter defining a lumen, and a vessel closure device configured to be received within the lumen of the catheter. In some examples, the vessel closure devices described herein may include an elongated flexible member, and one or more anchors attached to the elongated flexible member. Each anchor may comprise an anchor head configured to be introduced into a wall of a target vessel. Once an anchor head is introduced into a wall of the target vessel, a proximal pulling force may be applied to the elongated flexible member, thereby causing the lumen of the target vessel to collapse. In some examples, an adhesive or other treatment material may be delivered to the treatment site. Also described herein are methods of using the vessel closure device and the vessel closure systems.

In a first example, aspects of the disclosure relate to a vessel closure system that includes: a catheter configured to be introduced into a vessel of a patient, the catheter defining a catheter lumen; and a vessel closure device configured to be received within the catheter lumen, the closure device including: an elongated flexible member; and a plurality of anchors attached to the elongated flexible member, the anchors of the plurality of anchors being distributed along a length of the elongated flexible member, wherein each anchor includes an anchor head configured to be introduced into a wall of the vessel and engage with the wall of the vessel to cause the wall to move radially inward in response to a proximal pulling force applied to the elongated flexible member.

In a second example relating to the vessel closure system of the first example, each anchor head of the plurality of anchor heads is configured to engage with the wall of the vessel at one attachment point to cause the vessel wall to move in response to a proximal pulling force applied to the elongated flexible member while the anchor head is engaged with the vessel wall at only the one attachment point.

In a third example relating to the vessel closure system of the first example or the second example, each anchor head of the plurality of anchor heads is configured to be introduced entirely through the wall of the vessel.

In a fourth example relating to the vessel closure system of the third example each anchor head of the plurality of anchor heads has a first end and a second end opposite the first end, the first end and the second end of the anchor head being configured to be introduced through the wall of the vessel.

In a fifth example relating to the vessel closure system of any of the first through fourth examples, each anchor head of the plurality of anchor heads has a first end and a second end opposite the first end, at least one of the first end or the second end of the anchor head defining a sharp point configured to pierce through the wall of the vessel.

In a sixth example relating to the vessel closure system of the fifth example, both the first end and the second end of the anchor head define the sharp point.

In a seventh example relating to the vessel closure system of the fifth example, each anchor head of the plurality of anchor heads further includes a barb.

In an eighth example relating to the vessel closure system of any of the first through seventh examples, each anchor of the plurality of anchors defines a T-shape.

In a ninth example relating to the vessel closure system of the eighth example, each anchor of the plurality of anchors further includes an anchor tether mechanically connected to the respective anchor head, the anchor tether extending at a non-parallel angle relative to a longitudinal axis of the anchor head, the tether and the anchor head defining the T-shape.

In a tenth example relating to the vessel closure system of any of the first through ninth examples, each anchor of the plurality of anchors is collapsible toward the elongated flexible member under a biasing force.

In an eleventh example relating to the vessel closure system of any of the first through tenth examples, each anchor head of the plurality of anchor heads has a greater cross-sectional dimension than the elongated flexible member, the cross-sections being taken perpendicular to respective longitudinal axes of the anchor head and elongated flexible member.

In a twelfth example relating to the example of the vessel closure system of any of the first through eleventh examples, the plurality of anchors is configured to biodegrade within the patient or to be bioabsorbable by the patient.

In a thirteenth example relating to the vessel closure system of the twelfth example, each anchor of the plurality of anchors includes one of polylactic acid (PLLA), poly(lactic-co-glycolic) acid (PLGA), or a polysaccharide.

In a fourteenth example relating to the vessel closure system of any of the first through thirteenth examples, each anchor of the plurality of anchors includes at least one of high-density polyethylene (HDPE), polyester, nitinol, or stainless steel.

In a fifteenth example relating to the vessel closure system of any of the first through fourteenth examples, each anchor of the plurality of anchors includes an echogenic or radiopaque material.

In a sixteenth example relating to the vessel closure system of the fifteenth example, the echogenic material includes at least one of titanium dioxide ($TiO_2$), platinum, or a platinum alloy.

In a seventeenth example relating to the vessel closure system of any of the first through sixteenth examples, the vessel closure system further includes a sclerosing agent on at least one anchor head of the plurality of anchors.

In an eighteenth example relating to the vessel closure system of any of the first through seventeenth examples, the anchors of the plurality of anchors are separated from each other along the elongated flexible member by about 5 millimeters to about 30 millimeters.

In a nineteenth example relating to the vessel closure system of any of the first through eighteenth examples, the anchors of the plurality of anchors are evenly distributed along a length of the elongated flexible member.

In a twentieth example relating to the vessel closure system of any of the first through nineteenth examples, the anchors of the plurality of anchors are unevenly distributed along a length of the elongated flexible member.

In a twenty-first example relating to the vessel closure system of any of the first through twentieth examples, the vessel closure system further includes a needle configured to be received within the catheter lumen, the needle defining a needle lumen configured to receive at least a part of the vessel closure device and deliver the anchor head of at least one anchor of the plurality of anchors through the vessel wall.

In a twenty-second example relating to the vessel closure system of the twenty-first example, the needle defines a sharp distal end configured to cut through the vessel wall.

In a twenty-third example relating to the vessel closure system of the twenty-first example, the needle defines a curved distal portion configured to extend away from the catheter when the needle exits the catheter lumen.

In a twenty-fourth example relating to the vessel closure system of the twenty-first example, the anchor head has a smaller cross-sectional dimension than a diameter of the needle lumen, the cross-section being taken in a direction perpendicular to a longitudinal axis of the anchor head, and wherein the anchor head defines a length as measured parallel to the longitudinal axis of the anchor head that is greater than the diameter of the needle lumen.

In a twenty-fifth example relating to the vessel closure system of the twenty-first example, the needle lumen is sized to receive all of the anchors of the vessel closure device.

In a twenty-sixth example relating to the vessel closure system of any of the first through twenty-fifth examples, the elongated flexible member is devoid of a lumen.

In a twenty-seventh example relating to the vessel closure system of any of the first through twenty-sixth examples, a material of the elongated flexible member is configured to be biodegradable or bioabsorbable.

In a twenty-eighth example relating to the vessel closure system of the twenty-seventh example, the biodegradable or bioabsorbable material includes at least one of polylactic acid (PLLA), poly(lactic-co-glycolic acid) (PLGA), or a polysaccharide.

In a twenty-ninth example relating to the vessel closure system of any of the first through twenty-eighth examples, the elongated flexible member includes at least one of high-density polyethylene (HDPE), polyester, nitinol, or stainless steel.

In a thirtieth example relating to the vessel closure system of any of the first through twenty-ninth examples, the vessel closure system further includes a pusher member configured to be received within the catheter lumen and apply a force to at least one of the anchor heads to push the anchor head into the vessel wall.

In a thirty-first example relating to the vessel closure system of the thirtieth example, the pusher member is configured to engage with a proximal end of the elongated flexible member, wherein the pusher member and elongated flexible member are configured to be movable relative to the delivery catheter.

In a thirty-second example relating to the vessel closure system of any of the first through thirty-first examples, the elongated flexible member includes one or more markers configured to indicate a spacing between adjacent anchors of the plurality of anchors along the length of the elongated flexible member.

In a thirty-third example relating to the vessel closure system of any of the first through thirty-second examples, the catheter includes a first catheter, the system further including a second catheter configured to deliver a treatment material to a location within the vessel adjacent at least one anchor of the plurality of anchors, the first and second catheters being movable relative to each other.

In a thirty-fourth example relating to the vessel closure system of any of the first through thirty-third examples, the catheter lumen includes a first catheter lumen, the catheter further including a second catheter lumen configured to deliver a treatment material to a location within the vessel adjacent at least one anchor of the plurality of anchors.

In a thirty-fifth example relating to the vessel closure system of the thirty-fourth example, the vessel closure system further includes the treatment material, wherein the treatment material includes a medical adhesive.

In a thirty-sixth example, aspects of the disclosure relate to a vessel closure system that includes: a catheter body configured to be introduced into a vessel of a patient, the catheter body defining a catheter lumen; and a vessel closure device configured to be received within the catheter lumen, the vessel closure device including: an elongated flexible member; and at least one biodegradable or bioabsorbable anchor, wherein each anchor of the at least one anchor includes an anchor head configured to be introduced into a wall of the vessel and engage with the wall of the vessel to cause the vessel wall to move in response to a proximal pulling force applied to the elongated flexible member.

In a thirty-seventh example relating to the vessel closure system of the thirty-sixth example, the anchor head is configured to engage with the wall of the vessel at one attachment point to cause the vessel wall to move in response to a proximal pulling force applied to the elongated flexible member while the anchor head is engaged with the vessel wall at only the one attachment point.

In a thirty-eighth example relating to the vessel closure system of the thirty-sixth or the thirty-seventh example, the anchor head is configured to be introduced entirely through the wall of the vessel.

In a thirty-ninth example relating to the vessel closure system of the thirty-eighth example, the anchor head has a first end and a second end opposite the first end, the first end and the second end of the anchor head being configured to be introduced through the wall of the vessel.

In a fortieth example relating to the vessel closure system of any of the thirty-sixth through thirty-ninth examples, the anchor head has a first end and a second end opposite the first end, at least one of the first end or the second end of the anchor head defining a sharp point configured to pierce through the wall of the vessel.

In a forty-first example relating to the vessel closure system of the fortieth example, both the first end and the second end of the anchor head define the sharp point.

In a forty-second example relating to the vessel closure system of the fortieth example, the anchor head further includes a barb.

In a forty-third example relating to the vessel closure system of any of the thirty-sixth through fortieth examples, the at least one anchor defines a T-shape.

In a forty-fourth example relating to the vessel closure system of the forty-third example, the at least one anchor further includes an anchor tether mechanically connected to the respective anchor head, the anchor tether extending at a non-parallel angle relative to a longitudinal axis of the anchor head, the tether and the anchor head defining the T-shape.

In a forty-fifth example relating to the vessel closure system of any of the thirty-sixth through forty-fourth examples, the at least one anchor is collapsible toward the elongated flexible member under a biasing force.

In a forty-sixth example relating to the vessel closure system of any of the thirty-sixth through forty-fifth examples, the anchor head has a greater cross-sectional dimension than the elongated flexible member, the cross-sections being taken perpendicular to respective longitudinal axes of the anchor head and elongated flexible member.

In a forty-seventh example relating to the vessel closure system of any of the thirty-sixth through forty-sixth examples, the at least one anchor includes one of polylactic acid (PLLA), poly(lactic-co-glycolic) acid (PLGA), or a polysaccharide.

In a forty-eighth example relating to the vessel closure system of any of the thirty-sixth through forty-seventh examples, the at least one anchor includes an echogenic or radiopaque material.

In a forty-ninth example relating to the vessel closure system of the forty-eighth example, the echogenic or radiopaque material includes at least one of titanium dioxide (TiO$_2$), platinum, or a platinum alloy.

In a fiftieth example relating to the vessel closure system of any of the thirty-sixth through forty-ninth examples, the vessel closure system further includes a sclerosing agent on at the anchor head.

In a fifty-first example relating to the vessel closure system of any of the thirty-sixth through fiftieth examples, the vessel closure system further includes a needle configured to be received within the catheter lumen, the needle defining a needle lumen configured to receive at least a part of the vessel closure device and deliver the anchor head through the vessel wall.

In a fifty-second example relating to the vessel closure system of the fifty-first example, the needle defines a sharp distal end configured to cut through the vessel wall.

In a fifty-third example relating to the vessel closure system of the fifty-first example, the needle defines a curved distal portion configured to extend away from the catheter when the needle exits the catheter lumen.

In a fifty-fourth example relating to the vessel closure system of the fifty-first example, the anchor head has a smaller cross-sectional dimension than a diameter of the needle lumen, the cross-section being taken in a direction perpendicular to a longitudinal axis of the anchor head, and wherein the anchor head defines a length as measured parallel to the longitudinal axis of the anchor head that is greater than the diameter of the needle lumen.

In a fifty-fifth example relating to the vessel closure system of the fifty-first example, the needle lumen is sized to receive the at least one anchor of the vessel closure device.

In a fifty-sixth example relating to the vessel closure system of any of the thirty-sixth through fifty-fifth examples, the elongated flexible member is devoid of a lumen.

In a fifty-seventh example relating to the vessel closure system of any of the thirty-sixth through fifty-sixth examples, a material of the elongated flexible member is configured to be biodegradable or bioabsorbable.

In a fifty-eighth example relating to the vessel closure system of the fifty-seventh example, the biodegradable or bioabsorbable material includes at least one of polylactic acid (PLLA), poly(lactic-co-glycolic acid) (PLGA), or a polysaccharide.

In a fifty-ninth example relating to the vessel closure system of any of the thirty-sixth through fifty-fifth examples, the elongated flexible member includes at least one of high-density polyethylene (HDPE), polyester, nitinol, or stainless steel.

In a sixtieth example relating to the vessel closure system of any of the thirty-sixth through fifty-ninth examples, the vessel closure system further includes a pusher member configured to be received within the catheter lumen and apply a force to at least one of the anchor heads to push the anchor head into the vessel wall.

In a sixty-first example relating to the vessel closure system of the sixtieth example, the pusher member is configured to engage with a proximal end of the elongated flexible member, wherein the pusher member and elongated flexible member are configured to be movable relative to the delivery catheter.

In a sixty-second example relating to the vessel closure system of any of the thirty-sixth through sixty-first examples, the elongated flexible member includes one or more markers configured to indicate a spacing between adjacent anchors of the at least one anchor along the length of the elongated flexible member.

In a sixty-third example relating to the vessel closure system of any of the thirty-sixth through sixty-second examples, the catheter includes a first catheter, the system further including a second catheter configured to deliver a treatment material to a location within the vessel adjacent at least one anchor, the first and second catheters being movable relative to each other.

In a sixty-fourth example relating to the vessel closure system of any of the thirty-sixth through sixty-third examples, the catheter lumen includes a first catheter lumen, the catheter further including a second catheter lumen configured to deliver a treatment material to a location within the vessel adjacent at least one anchor.

In a sixty-fifth example relating to the vessel closure system of the sixty-fourth example, the vessel closure system further includes the treatment material, wherein the treatment material includes a medical adhesive.

In a sixty-sixth example relating to the vessel closure system of any of the thirty-sixth through sixty-fifth examples, the vessel closure device includes a plurality of anchors including the biodegradable or bioabsorbable anchor.

In a sixty-seventh example relating to the vessel closure system of the sixty-sixth example, each anchor of the plurality of anchors is biodegradable or bioabsorbable.

In a sixty-eighth example relating to the vessel closure system of the sixty-sixth or the sixty-seventh example, the anchors of the plurality of anchors are separated from each other along the elongated flexible member by about 5 millimeters to about 30 millimeters.

In a sixty-ninth example relating to the vessel closure system of any of the sixty-sixth through sixty-eighth examples, the anchors of the plurality of anchors are evenly distributed along a length of the elongated flexible member.

In a seventieth example relating to the vessel closure system of any of the sixty-sixth through sixty-eighth examples, the anchors of the plurality of anchors are unevenly distributed along a length of the elongated flexible member.

In a seventy-first example, aspects of this disclosure relate to a method that includes: introducing a vessel closure device into a vessel of a patient through a catheter lumen of a catheter, the vessel closure device including: an elongated flexible member; and a plurality of anchors attached to the elongated flexible member, the anchors of the plurality of anchors being distributed along a length of the elongated flexible member, wherein each anchor comprises an anchor head configured to be introduced into a wall of the vessel and engage with the wall of the vessel to cause the wall to move in response to a proximal pulling force applied to the elongated flexible member; introducing the anchor head of at least one of the anchors of the plurality of anchors into the wall of the vessel; and after introducing the anchor head into the wall of the vessel, pulling the elongated flexible member proximally to cause the wall of the vessel to move radially inward.

In a seventy-second example relating to the method of the seventy-first example, each anchor head of the plurality of anchor heads is configured to engage with the wall of the vessel at one attachment point to cause the vessel wall to move in response to a proximal pulling force applied to the elongated flexible member while the anchor head is engaged with the vessel wall at only the one attachment point.

In a seventy-third example relating to the method of the seventy-first example or the seventy-second example, each anchor head of the plurality of anchor heads is configured to be introduced entirely through the wall of the vessel.

In a seventy-fourth example relating to the method of any of the seventy-first through seventy-third examples each anchor head of the plurality of anchor heads has a first end and a second end opposite the first end, the first end and the second end of the anchor head being configured to be introduced through the wall of the vessel.

In a seventy-fifth example relating to the method of any of the seventy-first through seventy-fourth examples, each anchor head of the plurality of anchor heads has a first end and a second end opposite the first end, at least one of the first end or the second end of the anchor head defining a sharp point configured to pierce through the wall of the vessel.

In a seventy-sixth example relating to the method of the seventy-fifth example, both the first end and the second end of the anchor head define the sharp point.

In a seventy-seventh example relating to the method of any of the seventy-first through seventy-sixth examples, each anchor head of the plurality of anchor heads further includes a barb.

In a seventy-eighth example relating to the method of any of the seventy-first through seventy-seventh examples, each anchor of the plurality of anchors defines a T-shape.

In a seventy-ninth example relating to the method of the seventy-eighth example, each anchor of the plurality of anchors further includes an anchor tether mechanically connected to the respective anchor head, the anchor tether extending at a non-parallel angle relative to a longitudinal axis of the anchor head, the tether and the anchor head defining the T-shape.

In an eightieth example relating to the method of any of the seventy-first through seventy-ninth examples, each anchor of the plurality of anchors is collapsible toward the elongated flexible member under a biasing force.

In an eighty-first example relating to the method of any of the seventy-first through eightieth examples, each anchor head of the plurality of anchor heads has a greater cross-sectional dimension than the elongated flexible member, the cross-sections being taken perpendicular to respective longitudinal axes of the anchor head and elongated flexible member.

In an eighty-second example relating to the example of the method of any of the seventy-first through eighty-first examples, at least one of the elongated flexible member and the plurality of anchors is configured to biodegrade within the patient or to be bioabsorbable by the patient.

In an eighty-third example relating to the method of the eighty-second example, each anchor of the plurality of anchors includes one of polylactic acid (PLLA), poly(lactic-co-glycolic) acid (PLGA), or a polysaccharide.

In an eighty-fourth example relating to the method of any of the seventy-first through eighty-third examples, each anchor of the plurality of anchors includes at least one of high-density polyethylene (HDPE), polyester, nitinol, or stainless steel.

In an eighty-fifth example relating to the method of any of the seventy-first through eighty-fourth examples, each anchor of the plurality of anchors includes an echogenic or radiopaque material.

In an eighty-sixth example relating to the method of the eighty-fifth example, the echogenic or radiopaque material includes at least one of titanium dioxide ($TiO_2$), platinum, or a platinum alloy.

In an eighty-seventh example relating to the method of any of the seventy-first through eighty-sixth examples, the vessel closure system further includes a sclerosing agent on at least one anchor head of the plurality of anchors.

In an eighty-eighth example relating to the method of any of the seventy-first through eighty-seventh examples, the anchors of the plurality of anchors are separated from each other along the elongated flexible member by about 5 millimeters to about 30 millimeters.

In an eighty-ninth example relating to the method of any of the seventy-first through eighty-eighth examples, the anchors of the plurality of anchors are evenly distributed along a length of the elongated flexible member.

In a ninetieth example relating to the method of any of the seventy-first through eighty-ninth examples, the anchors of the plurality of anchors are unevenly distributed along a length of the elongated flexible member.

In a ninety-first example relating to the method of any of the seventy-first through ninetieth examples, introducing the closure device into the vessel of the patient includes advancing the closure device through a needle lumen of a needle, the needle lumen being configured to receive at least a part of the closure device.

In a ninety-second example relating to the method of the ninety-first example, the needle defines a sharp distal end configured to cut through the vessel wall.

In a ninety-third example relating to the method of the ninety-first example, the needle defines a curved distal portion configured to extend away from the catheter when the needle exits the catheter lumen.

In a ninety-fourth example relating to the method of the ninety-first example, the anchor head has a smaller cross-sectional dimension than a diameter of the needle lumen, the cross-section being taken in a direction perpendicular to a longitudinal axis of the anchor head, and wherein the anchor head defines a length as measured parallel to the longitudinal axis of the anchor head that is greater than the diameter of the needle lumen.

In a ninety-fifth example relating to the method of the ninety-first example, the needle lumen is sized to receive all of the anchors of the vessel closure device.

In a ninety-sixth example relating to the method of any of the seventy-first through ninety-fifth examples, the elongated flexible member is devoid of a lumen.

In a ninety-seventh example relating to the method of any of the seventy-first through ninety-sixth examples, a material of the elongated flexible member is configured to be biodegradable or bioabsorbable.

In a ninety-eighth example relating to the method of the ninety-seventh example, the biodegradable or bioabsorbable material includes at least one of polylactic acid (PLLA), poly(lactic-co-glycolic acid) (PLGA), or a polysaccharide.

In a ninety-ninth example relating to the method of any of the seventy-first through ninety-eighth examples, the elongated flexible member includes at least one of high-density polyethylene (HDPE), polyester, nitinol, or stainless steel.

In a hundredth example relating to the method of any of the seventy-first through ninety-ninth examples, the method further includes pushing the anchor head into the wall of the vessel with a pusher member.

In a hundred-and-first example relating to the method of the hundredth example, the pusher member is configured to engage with a proximal end of the elongated flexible member, wherein the pusher member and elongated flexible member are configured to be movable relative to the delivery catheter.

In a hundred-and-second example relating to the method of any of the seventy-first through hundred-and-first examples, pulling the elongated flexible member proximally comprises pulling the closure device proximally by a distance defined by a plurality of markers on a proximal portion of the elongated flexible member.

In a hundred-and-third example relating to the method of the hundred-and-second example, the plurality of markers corresponds to a distance between adjacent anchors of the plurality of anchors along the length of the flexible elongated member.

In a hundred-and-fourth example relating to the method of any of the seventy-first through hundred-and-third examples, the catheter includes a first catheter, the system further including a second catheter configured to deliver a treatment material to a location within the vessel adjacent at least one anchor of the plurality of anchors, the first and second catheters being movable relative to each other.

In a hundred-and-fifth example relating to the method of any of the seventy-first through hundred-and-fourth examples, the catheter lumen includes a first catheter lumen, the catheter further including a second catheter lumen configured to deliver a treatment material to a location within the vessel adjacent at least one anchor of the plurality of anchors.

In a hundred-and-sixth example relating to the method of any of the seventy-first through hundred-and fifth examples, the method further includes introducing the catheter into the vessel of the patient.

In a hundred-and-seventh example relating to the method of any of the seventy-first through hundred-and-sixth examples, the method further includes introducing the anchor head into the wall of the vessel comprises introducing the anchor head entirely through the vessel wall such that the catheter and the anchor head are on opposite sides of the vessel wall.

In a hundred-and-eighth example relating to the method of any of the seventy-first through hundred-and-sixth examples, introducing the anchor head into the wall of the vessel includes introducing the anchor head into the wall of the vessel such that the anchor head is at least partially embedded in the wall of the vessel.

In a hundred-and-ninth example relating to the method of any of the seventy-first through hundred-and-eighth examples, introducing the anchor head into the wall of the vessel comprises introducing the anchor head into the wall of the vessel at a treatment site, the method further comprising delivering a treatment material to the vessel at a position adjacent the treatment site.

In a hundred-and-tenth example relating to the method of the hundred-and-ninth example, pulling the elongated flexible member proximally comprises pulling the elongated flexible member proximally to cause the wall of the vessel to move radially inward to define collapsed walls of the vessel at the treatment site such that the treatment material is between the collapsed walls of the vessel.

In a hundred-and-eleventh example relating to the method of any of the seventy-first through hundred-and-tenth examples, the method further includes after pulling the elongated flexible member proximally to cause the wall of the vessel to move radially inward, cutting the elongate flexible member.

In a hundred-and-twelfth example relating to the method of any of the seventy-first through hundred-and-eleventh examples, introducing the anchor head into the wall of the vessel includes introducing a first anchor head into the wall of the vessel at a first treatment site, the method further including: after pulling the elongated flexible member proximally to cause the wall of the vessel to move radially inward, introducing a second anchor head of another anchor of the plurality of anchors into the wall of the vessel at a second treatment site; and after introducing the second anchor head into the wall of the vessel at the second treatment site, pulling the elongated flexible member proximally to cause the wall of the vessel to move radially inward at the second treatment site.

In a hundred-and-thirteenth example, aspects of the disclosure relate to a method including: introducing a closure device into a vessel of a patient through a catheter lumen of a catheter, the closure device comprising: an elongated flexible member; and at least one biodegradable or bioabsorbable anchor, wherein each anchor of the at least one anchor comprises an anchor head configured to be introduced into a wall of the vessel and engage with the wall of the vessel to cause the vessel wall to move in response to a proximal pulling force applied to the elongated flexible member; introducing the anchor head into the wall of the vessel at a treatment site; and after introducing the anchor head into the wall of the vessel at the treatment site, pulling the elongated flexible member proximally to cause the wall of the vessel to move radially inward.

In a hundred-and-fourteenth example relating to the method of the hundred-and-thirteenth example, the anchor head is configured to engage with the wall of the vessel at one attachment point to cause the vessel wall to move in response to a proximal pulling force applied to the elongated flexible member while the anchor head is engaged with the vessel wall at only the one attachment point.

In a hundred-and-fifteenth example relating to the method of the hundred-and-thirteenth or the hundred-and-fourteenth example, the anchor head is configured to be introduced entirely through the wall of the vessel.

In a hundred-and-sixteenth example relating to the method of any of the hundred-and-thirteenth through hundred-and-fifteenth examples, the anchor head has a first end and a second end opposite the first end, the first end and the second end of the anchor head being configured to be introduced through the wall of the vessel.

In a hundred-and-seventeenth example relating to the method of any of the hundred-and-thirteenth through hundred-and-sixteenth examples, the anchor head has a first end and a second end opposite the first end, at least one of the first end or the second end of the anchor head defining a sharp point configured to pierce through the wall of the vessel.

In a hundred-and-eighteenth example relating to the method of the hundred-and-seventeenth example, both the first end and the second end of the anchor head define the sharp point.

In a hundred-and-nineteenth example relating to the method of any of the hundred-and-thirteenth through hundred-and-eighteenth examples, the anchor head further includes a barb.

In a hundred-and-twentieth example relating to the method of any of the hundred-and-thirteenth through hundred-and-nineteenth examples, the at least one anchor defines a T-shape.

In a hundred-and-twenty-first example relating to the method of the hundred-and-twentieth example, the at least one anchor further includes an anchor tether mechanically connected to the respective anchor head, the anchor tether extending at a non-parallel angle relative to a longitudinal axis of the anchor head, the tether and the anchor head defining the T-shape.

In a hundred-and-twenty-second example relating to the method of any of the hundred-and-thirteenth through hundred-and-twenty-first examples, the at least one anchor is collapsible toward the elongated flexible member under a biasing force.

In a hundred-and-twenty-third example relating to the method of any of the hundred-and-thirteenth through hundred-and-twenty-second examples, the anchor head has a greater cross-sectional dimension than the elongated flexible member, the cross-sections being taken perpendicular to respective longitudinal axes of the anchor head and elongated flexible member.

In a hundred-and-twenty-fourth example relating to the method of any of the hundred-and-thirteenth through hundred-and-twenty-third examples, the at least one anchor includes one of polylactic acid (PLLA), poly(lactic-co-glycolic) acid (PLGA), or a polysaccharide.

In a hundred-and-twenty-fifth example relating to the method of any of the hundred-and-thirteenth through hundred-and-twenty-fourth examples, the at least one anchor includes an echogenic or radiopaque material.

In a hundred-and-twenty-sixth example relating to the method of the hundred-and-twenty-fifth example, the echogenic or radiopaque material includes at least one of titanium dioxide ($TiO_2$), titanium, or a titanium alloy.

In a hundred-and-twenty-seventh example relating to the method of any of the hundred-and-thirteenth through hundred-and-twenty-sixth examples, the vessel closure system further includes a sclerosing agent on at the anchor head.

In a hundred-and-twenty-eighth example relating to the method of any of the hundred-and-thirteenth through hundred-and-twenty-seventh examples, the method further includes introducing the closure device into the vessel of the patient includes advancing the closure device through a needle lumen of a needle, the needle lumen being configured to receive at least a part of the closure device.

In a hundred-and-twenty-ninth example relating to the method of the hundred-and-twenty-eighth example, the needle defines a sharp distal end configured to cut through the vessel wall.

In a hundred-and-thirtieth example relating to the method of the hundred-and-twenty-eighth example, the needle defines a curved distal portion configured to extend away from the catheter when the needle exits the catheter lumen.

In a hundred-and-thirty-first example relating to the method of the hundred-and-twenty-eighth example, the anchor head has a smaller cross-sectional dimension than a diameter of the needle lumen, the cross-section being taken in a direction perpendicular to a longitudinal axis of the anchor head, and wherein the anchor head defines a length as measured parallel to the longitudinal axis of the anchor head that is greater than the diameter of the needle lumen.

In a hundred-and-thirty-second example relating to the method of the hundred-and-twenty-eighth example, the needle lumen is sized to receive all of the anchors of the vessel closure device.

In a hundred-and-thirty-third example relating to the method of any of the hundred-and-thirteenth through hundred-and-thirty-second examples, the elongated flexible member is devoid of a lumen.

In a hundred-and-thirty-fourth example relating to the vessel closure system of any of the hundred-and-thirteenth through hundred-and-thirty-third examples, a material of the elongated flexible member is configured to be biodegradable or bioabsorbable.

In a hundred-and-thirty-fifth example relating to the method of the hundred-and-thirty-fourth example, the biodegradable or bioabsorbable material includes at least one of polylactic acid (PLLA), poly(lactic-co-glycolic acid) (PLGA), or a polysaccharide.

In a hundred-and-thirty-sixth example relating to the method of any of the hundred-and-thirteenth through hundred-and-thirty-third examples, the elongated flexible member includes at least one of high-density polyethylene (HDPE), polyester, nitinol, or stainless steel.

In a hundred-and-thirty-seventh example relating to the method of any of the hundred-and-thirteenth through hundred-and-thirty-sixth examples, the method further includes pushing the anchor head into the wall of the vessel with a pusher member.

In a hundred-and-thirty-eighth example relating to the method of the hundred-and-thirty-seventh example, the pusher member is configured to engage with a proximal end of the elongated flexible member, wherein the pusher member and elongated flexible member are configured to be movable relative to the delivery catheter.

In a hundred-and-thirty-ninth example relating to the method of any of the hundred-and-thirteenth through hundred-and-thirty-eighth examples, pulling the elongated flexible member proximally comprises pulling the closure device proximally by a distance defined by a plurality of markers on a proximal portion of the elongated flexible member.

In a hundred-and-fortieth example relating to the method of the hundred-and-thirty-ninth example, the plurality of markers corresponds to a distance between adjacent anchors of the plurality of anchors along the length of the flexible elongated member.

In a hundred-and-forty-first example relating to the method of any of the hundred-and-thirteenth through hundred-and-fortieth examples, the catheter includes a first catheter, the system further including a second catheter configured to deliver a treatment material to a location within the vessel adjacent at least one anchor of the plurality of anchors, the first and second catheters being movable relative to each other.

In a hundred-and-forty-second example relating to the method of any of the hundred-and-thirteenth through hundred-and-forty-first examples, the catheter lumen includes a first catheter lumen, the catheter further including a second catheter lumen configured to deliver a treatment material to a location within the vessel adjacent at least one anchor of the plurality of anchors.

In a hundred-and-forty-third example relating to the method of the hundred-and-forty-second example, the vessel closure system further includes the treatment material, wherein the treatment material includes a medical adhesive.

In a hundred-and-forty-fourth example relating to the method of any of the hundred-and-thirteenth through hundred-and-forty-third examples, the vessel closure device includes a plurality of anchors including the biodegradable or bioabsorbable anchor.

In a hundred-and-forty-fifth example relating to the method of the hundred-and-forty-third example, each anchor of the plurality of anchors is biodegradable or bioabsorbable.

In a hundred-and-forty-sixth example relating to the method of the hundred-and-forty-fourth and/or the hundred-and-forty-fifth example, the anchors of the plurality of anchors are separated from each other along the elongated flexible member by about 5 millimeters to about 30 millimeters.

In a hundred-and-forty-seventh example relating to the method of any of the hundred-and-forty-fourth through hundred-and-forty-sixth examples, the anchors of the plurality of anchors are evenly distributed along a length of the elongated flexible member.

In a hundred-and-forty-eighth example relating to the method of any of the hundred-and-forty-fourth through hundred-and-forty-seventh examples, the anchors of the plurality of anchors are unevenly distributed along a length of the elongated flexible member.

In a hundred-and-forty-ninth example relating to the method of any of the hundred-and-thirteenth through hundred-and-forty-eighth examples, the method further includes introducing the catheter into the vessel of the patient.

In a hundred-and-fiftieth example relating to the method of any of the hundred-and-thirteenth through hundred-and-forty-ninth examples, the method further includes introducing the anchor head into the wall of the vessel comprises introducing the anchor head entirely through the vessel wall such that the catheter and the anchor head are on opposite sides of the vessel wall.

In a hundred-and-fifty-first example relating to the method of any of the hundred-and-thirteenth through hundred-and-fiftieth examples, introducing the anchor head into the wall of the vessel includes introducing the anchor head into the wall of the vessel such that the anchor head is at least partially embedded in the wall of the vessel.

In a hundred-and-fifty-second example relating to the method of any of the hundred-and-thirteenth through hundred-and-fifty-first examples, introducing the anchor head into the wall of the vessel comprises introducing the anchor head into the wall of the vessel at a treatment site, the method further comprising delivering a treatment material to the vessel at a position adjacent the treatment site.

In a hundred-and-fifty-third example relating to the method of any of the hundred-and-thirteenth through hundred-and-fifty-second examples, pulling the elongated flexible member proximally comprises pulling the elongated flexible member proximally to cause the wall of the vessel to move radially inward to define collapsed walls of the vessel at the treatment site such that the treatment material is between the collapsed walls of the vessel.

In a hundred-and-fifty-fourth example relating to the method of any of the hundred-and-thirteenth through hundred-and-fifty-third examples, the method further includes after pulling the elongated flexible member proximally to cause the wall of the vessel to move radially inward, cutting the elongate flexible member.

In a hundred-and-fifty-fifth example relating to the method of any of the hundred-and-thirteenth through hundred-and-fifty-fourth examples, introducing the anchor head into the wall of the vessel includes introducing a first anchor head into the wall of the vessel at a first treatment site, the method further including: after pulling the elongated flexible member proximally to cause the wall of the vessel to move radially inward, introducing a second anchor head of another anchor of the plurality of anchors into the wall of the vessel at a second treatment site; and after introducing the second anchor head into the wall of the vessel at the second treatment site, pulling the elongated flexible member proximally to cause the wall of the vessel to move radially inward at the second treatment site.

In a hundred-and-fifty-sixth example relating to the vessel closure devices or methods of any of the first through hundred-and-fifty-fifth examples, the anchor head is more rigid than an elongated flexible member.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 3 is a cross-sectional view of an example vessel closure system including a needle and a vessel closure device received within a lumen of the needle, where the cross-section is taken along a longitudinal axis of the needle.

FIG. 4 is a side view of an example vessel closure system including a vessel closure device and a pusher member engaged with a proximal end of the elongated flexible member.

FIG. 11A-11F are a series of cross-sectional views showing an example vessel closure system being operated in accordance with techniques described with respect to the example method of FIG. 10.

Figure 1:
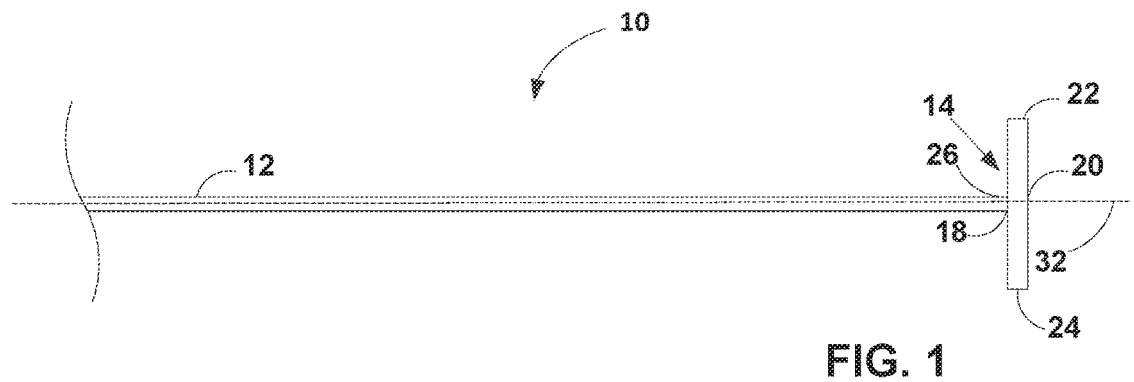
FIG. 1 is a side view of an example vessel closure device including an elongated flexible member and an anchor disposed at a distal end of the elongated flexible member, where the anchor includes an anchor head.

The details of one or more examples of this disclosure are set forth in the accompanying drawings and the description below. Other features, objects, and advantages of this disclosure will be apparent from the description and drawings, and from the claims.

DETAILED DESCRIPTION

Healthy leg veins within the human body contain valves that allow blood to move in one direction from the lower limbs toward the heart. These valves open when blood is flowing toward the heart, and close to prevent the backward flow of blood. Venous reflux occurs when valves cannot close properly due to, for example, the weakening and enlargement of the vessel over time leading to venous reflux and impaired drainage of venous blood from the vessels and legs. Venous reflux may be most common in the superficial veins such as the great saphenous vein, which runs from the top of the foot to the groin, where it originates at a deep vein. Options for treating venous reflux include treating the symptom at the source such as, for example, the great saphenous vein, by closing off the vessel to thereby force the blood to be redirected into other veins. Vessel closure also may be referred to as vessel coaptation, as in some examples vessel closure may involve collapsing the vessel until opposite sides of the vessel wall are brought into contact with one another.

In some examples, vessel closure may be performed by introducing an adhesive material into the vasculature of a patient and adhering the vessel closed. For example, a clinician may introduce and advance a delivery catheter through the vasculature of a patient to a target treatment site and deliver an aliquot of adhesive at the target treatment site. The clinician may then manually compress the site from the outside of the body, such as by using an ultrasound probe or using another device or the clinician's hand. The applied compression may cause the target vessel to collapse at the location of the delivered adhesive. Compression is maintained until the adhesive cures to an extent sufficient to ablate the target treatment site, which can take at least several minutes. In examples in which the target vessel is located in a relatively superficial portion of the vasculature, compression of the treatment site may be adequate to achieve collapse of the target vessel. However, other treatment sites located within the body of a patient, such as, for example, within the abdominal and pelvic cavities, within deep muscle tissue, the cranial or thoracic regions, and similar regions, may be challenging or impossible to collapse via and external compression force. For example, external pressure may not apply sufficient pressure to the target vessel, for example, if the vessel is deeper than expected, or may vary depending on the treating physician. Further, a treating physician may have to apply pressure for a relatively long period, thus extending the procedure time.

In some examples, alternative vessel closure devices and systems may be used to close vessels located within such challenged regions. For example, such regions may be treated by implanting an embolic, such as one or more coils or a vascular plug, within the vessel of the patient. Coils may close the vessel via thrombosis by causing the formation of a clot that blocks the vessel. However, coils and vascular plugs can be challenging to initially anchor to the wall of the vessel, such as in vessels having relatively high blood flow. In such high-flow vessels, temporary restriction of blood flow prior to anchoring a coil or plug to a vessel wall may be desirable in order to achieve reliable embolization from the coils or plugs. In addition, vessel closures achieved via thrombosis may be susceptible to re-cannulation over time, which may necessitate revision.

This disclosure describes example endovenous vessel closure devices and systems that can be used mechanically to collapse a target vessel of a patient from inside the vessel without the need for an external compressive force, although an external compressive force may be used in conjunction with the vessel closure devices and systems if desired. The example vessel closure systems described herein may include a vessel closure device that includes one or more anchors disposed along an elongated flexible member, each anchor including an anchor head. The one or more anchors may be delivered to and anchored (e.g., inserted partially through or completely through) to the wall of a vessel at a target treatment site. The vessel closure device may then be pulled from within the vessel (for example, in a proximal direction) to engage the anchor head with the vessel and to forcibly collapse the vessel at the target treatment site.

In some examples, the endovenous vessel closure devices can be used to mechanically collapse or coapt a target vessel of a patient from inside the vessel with or without the application of an external compression force by the clinician during the treatment procedure. For example, the vessel closure devices described herein may help to mechanically collapse or coapt a vessel from within the body of a patient thereby reducing the amount or the need for an external compression force by a clinician to close the vessel. In some cases, it may be advantageous for a clinician to be able to collapse or coapt a vessel without the application of an external compression force. For example, clinician fatigue may be reduced where the clinician need not manually apply an external compression force to collapse a target vessel. Further, the vessel closure device may provide more consistent closing forces that external compression forces, which may vary depending on the clinician and/or the depth of the vessel. In addition, the vessel closure devices and systems described herein can be used to collapse or coapt vessels located within deep portions of the anatomy that are not collapsible by the external application of compression. The vessel closure devices described herein may provide temporary, reversible, or permanent vessel closures. In some examples, the vessel closure systems described herein also may include a delivery catheter configured to supply treatment material (e.g., a medical adhesive) to aid in maintaining closure of the vessel at the target treatment site.

While the present disclosure describes the endovenous vessel closure devices primarily in the context of treating venous reflux within portions of the deep venous system (e.g., within the pelvic region or portions of the vasculature superficial to deep perforator veins), the devices of the present disclosure may also be used for collapsing other vessels within the body of a patient and/or treating other ailments including, for example, venous insufficiency/varicose veins of the upper and/or lower extremities, esophageal varices, gastric varices, hemorrhoidal varices, venous lakes, varicocele, Klippel-Trenanay syndrome, telangiectasias, aneurysms, arterio-venous malformations (AVM), embolization of tumors or bleeding vessels, lymphedema, vascular and nonvascular fistulas, closure of fallopian tubes for sterilization, or the like.

Figure 2A:
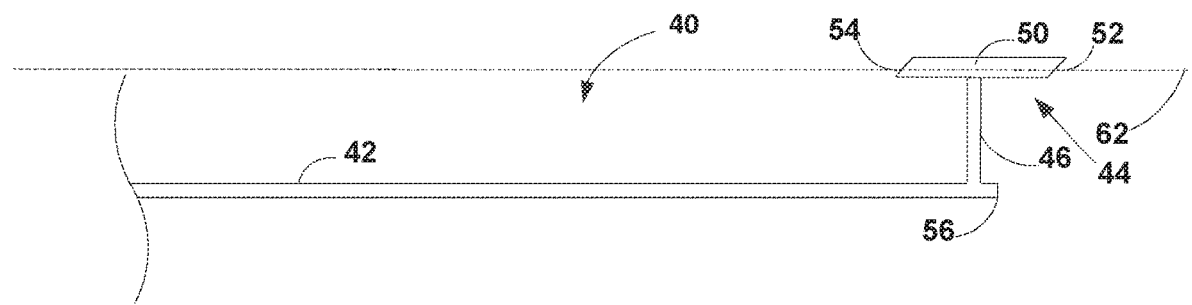
FIG. 2A is a side view of another example vessel closure device including an elongated flexible member and an anchor disposed at a distal end of the elongated flexible member, where the anchor head includes an anchor head and an anchor tether.
Figure 2B:
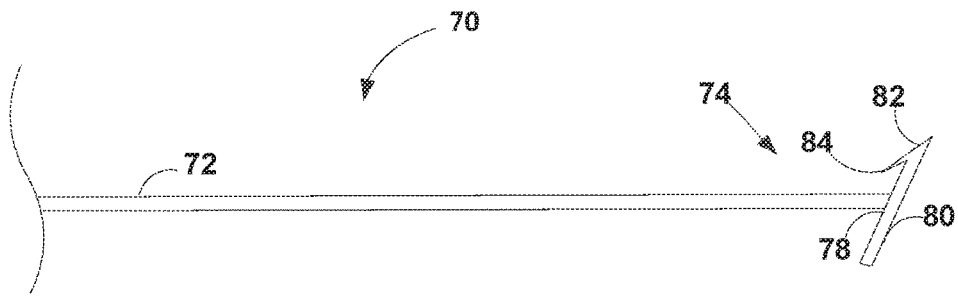
FIG. 2B is a side view of another example vessel closure device including an elongated flexible member and an anchor disposed at a distal end of the elongated flexible member, where the anchor includes an anchor head that includes at least one barb.

FIGS. 1-2B are side views of example vessel closure devices 10, 40, 70 that may be used alone or in conjunction with one or more of the vessel closure systems described herein. FIG. 1 is a side view of an example vessel closure device 10 configured to assist with the closing of a target vessel within the body of a patient. The vessel closure device 10 includes an elongated flexible member 12 and at least one anchor 14 disposed at a distal end 26 of the elongated flexible member 12. The anchor 14 includes an anchor head 20 configured to be embedded in or introduced entirely through the wall of a target vessel and engage with the wall. Once anchored to the vessel of a patient, a proximal pulling force (e.g., retracting force) may be applied to the elongated flexible member 12 to engage the anchor head 20 with the vessel wall (for example, forcing the anchor head 20 against the vessel wall) causing the vessel wall to move radially inward thereby closing or collapsing the inner lumen of the target vessel.

The elongated flexible member 12 may be relatively long and flexible compared to anchor 14. In some examples, elongated flexible member 12 may be non-self-supporting, although in other examples elongated flexible member 12 may have sufficient stiffness to be self-supporting and/or have sufficient rigidity to be pushable. In some examples, the elongated flexible member 12 may include a solid body (e.g., devoid of a lumen), coiled, braided, or constructed to include an inner lumen. In some examples, the elongated flexible member 12 may be sufficiently sized (e.g., about 5 cm to about 150 cm in length, the length being measured along a longitudinal axis 32 of the flexible member 12) to permit delivery of the anchor 14 to relatively distal portions within a vessel of a patient, or to a relatively superficial vessel (e.g., a relatively superficial perforator vessel), while still including a proximal portion that remains exterior to the patient's body that can be grasped and pulled by the clinician.

The anchor head 20 may be constructed to be relatively rigid compared to the elongated flexible member 12 to enable the anchor head 20 to be introduced into a wall of the vessel and engage with the wall when a clinician applies a pulling force to the elongated flexible member 12 so that the anchor head 20 does not disengage from the vessel wall. In some examples, the anchor head 20 may have a cylindrical or flattened profile that extends between a first end 22 and second end 24 along a longitudinal axis (e.g., perpendicular to the longitudinal axis 32 in FIG. 1). The length (e.g., distance between the first end 22 and the second end 24) and cross-sectional width of the anchor head 20 may be sized so that the first end 22 may be introduced through the vessel wall by orienting the anchor head 20 to be passed through the vessel wall along its longitudinal axis. The anchor head 20 may then expand off a longitudinal axis of the elongated flexible member 12 or of the anchor tether 46 once the anchor head has passed entirely through the vessel wall, so that a central axis of the anchor head 20 aligns within the vessel wall along the length of the anchor head 20 and so that the length of the anchor head 20 prevents the anchor 14 from being pulled back through the vessel wall. In some examples, the anchor head 20 may be configured to have a length (e.g., distance between the first end 22 and the second end 24) that is greater than the cross-sectional dimension of the elongated flexible member 12 as measured perpendicular to the longitudinal axis 32).

The various components of the vessel closure device 10 including the elongated flexible member 12 and the anchor 14 may be constructed from biocompatible materials. Suitable biocompatible materials may include, for example, non-biodegradable materials, such as high-density polyethylene (HDPE), polyester, nitinol, stainless steel, or other suitable non-biodegradable materials. In some examples, the anchor 14 may be formed at least partially of an echogenic or radiopaque material, such as titanium dioxide ($TiO_2$), titanium, a titanium alloy, or other suitable echogenic or radiopaque materials. Use of an echogenic, radiopaque, or the like material in the anchor 14 may aid in placement of the vessel closure device 10 at the target site. For example, during a procedure to place the vessel closure device 10, a clinician may apply an ultrasound or fluoroscopic device to the portion of the body through which vessel closure device 10 is being advanced, and monitor the location of the anchor 14 by the resulting image.

In some examples, permanent vessel closure may be desired, but the permanent implantation of the vessel closure device 10 may not be desired. In such examples, the vessel closure device 10 may be formed using one or more biodegradable materials and may be co-delivered to a treatment site in a target vessel with a treatment material, such as a non-biodegradable adhesive. The vessel closure device 10 may then be used to collapse or coapt the vessel from within the vessel to enable the treatment material to seal and occlude the vessel. Once accomplished, the vessel closure device 10 may dissolve and/or be absorbed over time by the body of a patient while the vessel remains closed. In such examples, one or more of the components of vessel closure device 10 may include biodegradable or bioabsorbable materials including, for example, polymeric materials such as polylactic acid (PLLA), poly(lactic-co-glycolic acid) (PLGA); polysaccharides; biodegradable or bioabsorbable metals such as a magnesium alloy or an iron alloy; or the like. By constructing the vessel closure device 10 using biodegradable or bioabsorbable materials, the vessel closure device 10 may be dissolved or absorbed by the patient's body over time. Although such materials may be referred to simply as "biodegradable" in some examples described herein, it will be understood that bioabsorbable materials also may be used in such examples.

The selection of the material from which the vessel closure device 10 is made may be selected based on one or more factors, such as the intended longevity of the vessel closure device 10 within the body. In some examples, a biodegradable or bioabsorbable material may be selected for one or more components of the vessel closure device 10 where impermanent placement of one or more of the components of the vessel closure device 10 is desired. For example, elongated flexile member 12, anchor 14 and portions thereof, or both may be constructed with biodegradable or bioabsorbable materials.

In examples where vessel closure device 10 includes a plurality of anchors, one or more or the respective anchors may include biodegradable or bioabsorbable materials. For example, anchor 14 may include a biodegradable or bioabsorbable material such as a polysaccharide that may be dissolved by the body over a relatively short duration of time (e.g., a few minutes) while the elongated flexile member 12 may be formed of a non-biodegradable material or biodegradable material that takes a greater duration of time to be dissolved or broken down by the body. Such a construction would allow a clinician to deploy anchor 14 and coapt the target vessel. The anchor 14 would then be dissolved shortly after coaptation allowing the clinician to remove the elongated flexile member 12 from the vessel before completing the procedure.

In some examples, the characteristics of the vessel closure device 10, such as dimensions and composition of the biodegradable material, may be designed based on a desired longevity of the vessel closure device 10 within the body. With respect to examples in which relatively short longevity of the vessel closure device 10 is desired, materials that rapidly biodegrade may be selected. For example, one or more portions of the vessel closure device may be configured to biodegrade within a matter of minutes, such as less than five minutes, less than ten minutes, or any other suitable length of time, such as a length of time sufficient to allow a treatment material to ablate a target vessel. Conversely, materials that more slowly biodegrade may be selected where relatively long-term implantation is desired. The longevity of a biodegradable material of the vessel closure device 10 also may depend upon the dimensions of the elongated flexible member 12 and the anchor 14 of the vessel closure device 10. For example, where the elongated flexible member 12 or the anchor 14 have relatively small cross-sectional dimensions, the components may exhibit a lower longevity in the body of the patient than examples in which the elongated flexible member 12 or the anchor 14 have relatively large cross-sectional dimensions. In some such examples, the biodegradable vessel closure device 10 may be co-delivered to a treatment site in a target vessel with a biodegradable treatment material, such as a biodegradable adhesive or sealant.

Additionally, or alternatively, the dimensions and composition of the vessel closure device 10 may be based on a dimension of the target site, such as a thickness of wall of a target vessel or a diameter of a target vessel to be collapsed. For example, a length of an anchor head, such as anchor head 20 of FIG. 1 or any other example anchor head described herein, may be designed to be positioned on the exterior of a vessel wall and engage with the vessel wall to coapt the vessel when a pulling force is applied. The length of the anchor head may be sized to help distribute the force along the sidewall of the vessel and prevent the anchor head from pulling back through the vessel wall. In other examples, a length of an anchor head, such as anchor head 20 of FIG. 1 or anchor head 80 (described below with respect to FIG. 2B), may be designed to extend through or only partially through the vessel wall of a target vessel, such that a portion of the anchor head remains embedded within the vessel wall. For example, where an anchor head (e.g., anchor head 80) extends only partially through the vessel wall, at least one end of the anchor head (e.g., first end 82 of FIG. 2B) becomes embedded within the vessel wall, such as for example within the medial layer, and does not extend completely through the wall of the target vessel when the anchor head has been delivered. In some such examples, the length and cross-sectional dimension of the anchor head may be sized small enough to enable the anchor head to be implanted within the vessel wall but not so large that the anchor head is delivered completely through the wall or becomes dislodged from the wall when a pulling force is applied.

In some examples, the anchor 14, portions of the elongated flexible member 12, or both may be coated with a sclerosing agent to enhance vessel closure, instead of or in addition to an adhesive or other treatment material that may be used in conjunction with the vessel closure device 10. Example sclerosing agents that may be coated onto one or more portions of the vessel closure device 10 may include detergent-based agents (e.g., sodium tetradecyl sulfate or ethanolamine oleate), or other categories of sclerosing agents capable of being coated onto the vessel closure device 10. In such examples, introduction of the vessel closure device 10 at the treatment site of the target vessel may cause the vessel to collapse or coapt such that the vessel wall adheres to itself, thereby closing the vessel.

As shown in FIG. 1, the anchor head 20 of the anchor 14 may be attached directly to the distal end 26 of the elongated flexible member 12 at an attachment point 18. In some such examples, the attachment point 18 may represent the midway point between the first end 22 and the second end 24. In some examples, the union between the anchor head 20 and the elongated flexible member 12 may be characterized as defining a "T-shape." As used herein a "T-shape" design is used to describe a non-parallel attachment between two components (e.g., the anchor head 20 and the elongated flexible member 12) such that at least one of the components (e.g., the anchor head 20) includes at least two ends extending different directions from the attachment point (e.g., the first and second ends 22, 24 extending away from the attachment point 18). In some examples, the T-shape may be characterized as forming generally perpendicular attachment between the two components, although other non-parallel angles are also included in the characterization of a T-shape. In some examples, the T-shape design may enable the anchor head 20 to engage with the vessel wall when a pulling force is applied to the elongated flexible member 12.

The anchor head 20 and the elongated flexible member 12 may be mechanically coupled using any suitable technique including, for example, adhesives, solder, welding, or other suitable fixation mechanisms. In other examples, the anchor head 20 may be formed integrally with the elongated flexible member 12, such as by incorporating the anchor head 20 into a material forming the elongated flexible member 12.

In other examples, the anchor head 20 may be attached indirectly to the elongated flexible member 12 using an anchor tether. For example, FIG. 2A is a side view of an example vessel closure device 40 configured to close a target vessel of a patient. As with the vessel closure device 10 of FIG. 1, the vessel closure device 40 includes an elongated flexible member 42 and an anchor 44 disposed near a distal end 56 of the elongated flexible member 42. The anchor 44 includes an anchor head 50 and an anchor tether 46 that couples the elongated flexible member 42 to the anchor head 50. In some examples, the anchor tether 46 may extend from the anchor head 50 at a non-parallel angle relative to a longitudinal axis 62 of the anchor head 50, such that the anchor tether 46 and the anchor head 50 define a T-shape (as described above). In such examples, the anchor tether 46 may be sufficiently flexible so as to be collapsible toward the longitudinal axis of the anchor head 50 and/or the elongated flexible member 42 under a biasing force to permit delivery of the anchor head 50 entirely or partially through the vessel wall of a patient without interference from the anchor tether 46. For example, as described further below with respect to FIG. 3, the vessel closure device 40 may be received within a needle such that the anchor head 50 co-axially aligns with the lumen of the needle and a biasing force applied to the anchor tether 46 causes the anchor tether 46 to collapse towards the anchor head 50 while the vessel closure device 40 is received within the needle.

The anchor 44 may be coupled to the elongated flexible member 42 using any suitable technique, such as by adhesives, solder, welding, or other suitable fixation mechanisms and/or elements. For example, opposite ends of the anchor tether 46 may be mechanically connected to respective portions of the elongated flexible member 42 and the anchor head 50. In other examples, the anchor tether 46 may be formed integrally with one or more of the anchor head 50 and the elongated flexible member 42, such as by incorporating the anchor tether 46 into a material forming either component. In examples in which the anchor tether 46 is formed integrally with only one of the anchor head 50 or elongated flexible member 42, the non-connected end of the anchor tether 46 may be mechanically connected to the appropriate component using any of the techniques described above. Anchor tether 46 may include one or more of the materials described above with respect to anchor 14 such as one or more biocompatible, biodegradable, or bioabsorbable materials.

The anchor tether 46 may be constructed using any suitable material. In some examples, the anchor tether 46 may be constructed using substantially the same materials as the anchor head 50 or the elongated flexible member 42. For example, in some examples, both the anchor head 50 and the anchor tether 46 may be formed using biodegradable or bioabsorbable materials.

In some examples, the anchor heads described herein (e.g., anchor head 20 of FIG. 1, anchor head 50 of FIG. 2A, or other example anchor heads), may be configured to aid in the advancement of the anchor head entirely or partially through the vessel wall. For example, as shown in FIG. 2A, at least one end (e.g., the first end 52 or the second end 54) may define a relatively sharp point (e.g., as compared to a blunt or rounded end), configured to assist with passing the anchor head 50 through the wall of a vessel. In some examples, only one of the first 52 and the second end 54 defines a sharp point, whereas in other examples, both the first end 52 and the second end 54 define a sharp point to enable the delivery of the anchor head 50 to be omnidirectional. In some examples, as described further below, the relatively sharp ends of the anchor head 50 may enable the anchor head to be introduced into a vessel wall without the aid of a delivery needle, although in some examples a needle may be used in conjunction with the sharp ends of the anchor head 50 to introduce the vessel closure device 40 into a vessel wall.

In some examples, the anchors of vessel closure devices described herein can include one or more surface protrusions that help retain the respective anchor to a vessel wall. For example, the anchor head 50 may include one or more barbs configured to help retain the anchor 44 within or entirely through the vessel wall. For example, FIG. 2B is a side view of another example vessel closure device 70 that includes an elongated flexible member 72, and an anchor 74 disposed at a distal end 78 of an elongated flexible member 72. The anchor 74 includes an anchor head 80 that defines a sharp point at a first end 82 and a barb 84 extending from the sharp point at the first end 82 towards the attachment point between the anchor head 80 and elongated flexible member 72. The barb 84 may interact with the vessel wall to help drive the anchor head 80 entirely or partially through the wall and allowing the barb 84 to engage with the wall to prevent subsequent removal of the anchor 74 when a pulling force is applied to the elongated flexible member 72.

In some examples, the anchor 74 may be configured so that the anchor head 80 may be introduced only partially through a vessel wall. For example, the anchor 74 may be introduced into a vessel wall until the first end 82 and the barb 84 have been embedded within the vessel wall such that a portion of the anchor head 80 remains within the lumen of the vessel. Although the vessel closure device 70 may be used at any treatment site, the configuration of the anchor 74 may be particularly useful where the target vessel is an artery, due to the greater thickness of artery walls relative to the walls of veins. For example, a target arterial wall may have sufficient thickness for the barb 84 to be embedded within the tissue thereof, and remain embedded within tissue of the artery, such as a media layer, upon application of a proximal pulling force to the elongated flexible member 72 in order to cause collapse or coaptation of the target vessel. In some examples, the barb 84 may have a roughened or otherwise textured surface to facilitate engagement of the barb 84 with the tissue of the vessel wall. As with the vessel closure devices 10 and 40 of FIGS. 1 and 2A, continued application of a proximal pulling force causes the anchor 74 to exert force against the vessel wall from the outer surface of the vessel wall or within the vessel wall (e.g., depending on whether anchor head 80 is introduced partially or entirely through the vessel wall), which results in the radially-inward collapse of the vessel wall and closure of the target vessel.

It will be understood from the description that the various structural features of the anchors 14, 44, 74 described above with respect to FIGS. 1, 2A, 2B (e.g., sharp points, anchor tethers, barbs, and the like) may be incorporated into any of the anchors or vessel closure devices described herein. For example, while anchor 14 of FIG. 1 is illustrated as having relatively blunt first and second ends 22, 24 on anchor head 20, in some examples, anchor 14 may include one or more sharp points or barbs on anchor head 20, an anchor tether, or combinations thereof. The structural features of the anchors described above are intended to be applicable to all vessel closure devices and anchors/anchor heads and not intended to limited the various structural features to a specific illustrated example.

In some examples, the vessel closure devices 10, 40, 70 may be configured to be delivered though a vessel wall using the assistance of one or more needles. For example, FIG. 3 is a cross-sectional view of an example vessel closure system 90 that includes a delivery needle 100 and an example vessel closure device 140 received within a lumen 110 of a needle 100, where the cross-section is taken along a longitudinal axis 116 of the needle 100. The vessel closure device 140 may be substantially similar to the vessel closure devices 10, 40, 70 described above. As shown in FIG. 3, the vessel closure device 140 includes an elongated flexible member 142 and at least one anchor 144 including an anchor head 150 and an anchor tether 146.

The anchor head 150 may be configured to be received co-axially within the lumen 110 of the needle 100 that defines a sharp point 114 at a distal end 112 configured to pierce the wall of the target vessel during a procedure to place an anchor 144 of the vessel closure device 140 within the vessel wall. The needle 100 may be formed from any suitable biocompatible material, such as nitinol (NiTi), stainless steel, or other suitable materials to enable the needle 100 to be navigated through the lumen of a vessel to a target treatment site and punctured partially or entirely through the vessel wall. The cross-sectional dimension (e.g., a diameter) of the lumen 110 may be sufficiently small to cause the anchor tether 146 of the anchor 144 to be biased radially inward toward the elongated flexible member 142 and the anchor head 150 when the vessel closure device 140 is received within the lumen 110. In some examples, the anchor tether 146 may be collapsed entirely when the vessel closure device 140 is received within the lumen 110, such that the anchor head 150 is brought into substantially parallel contact with the elongated flexible member 142 and the anchor head 150. In other examples, such as the example illustrated in FIG. 3, the anchor tether 146 may be only partially collapsed when vessel closure device is received within the lumen 110, such that the anchor head 150 may remain separated from the elongated flexible member 142.

Using the needle 100, the anchor 144 may be deposited entirely through the vessel wall such that the anchor head 150 is positioned on the exterior of the target vessel with the elongated flexible member 142 in the inner lumen of the vessel. Once the anchor head 150 has been delivered entirely through the vessel wall, and the anchor head 150 ejected from the lumen 110 of the needle 100, the elongated flexible member 142 may be pulled to enable the anchor 144 to engage a portion of the outer wall of the target vessel such that the length of the anchor head 150 prevents the anchor 144 from being pulled back through the puncture created by the needle 100. The engagement of the anchor head 150 with the outer wall of the target vessel causes the vessel wall to move radially inward in response to the application of a proximal pulling force to the elongated flexible member 142, as is more fully described and shown below.

In some examples, the dimensions of the needle 100 (and by extension, the cross-sectional dimension of the lumen 110) may be selected based on the relative size of the target vessel. For example, a relatively smaller size of a target vessel may require a correspondingly smaller gauge of the needle 100. In some examples, the needle 100 may be delivered to a target treatment site independently or with the aid of a delivery catheter, as described below with respect to FIGS. 4 and 5.

In other examples, the vessel closure devices described herein may be introduced into a vessel wall without the use of the needle 100. For example, FIG. 4 shows a vessel closure system 160 that includes a vessel closure device 170 and a pusher member 90 positioned proximally to an anchor 174. In some examples the vessel closure device 170 may be substantially similar to the vessel closure devices 40 or 70 described above such that at least one end of an anchor head 180 includes a sharp point so the anchor 174 may be delivered through the vessel wall of a patient without the aid of a delivery needle.

During introduction of the anchor 174 into the vessel wall, the pusher member 90 may be configured to engage with an elongated flexible member 172 or the anchor 174. A clinician may exert a pushing force on the pusher member 90, which is transmitted to the anchor 174. The force exerted by the clinician may then cause a sharp point of a first end 182 to pierce the interior of the vessel wall to drive the anchor 174 partially (e.g., in examples in which the anchor head 180 includes a barb 184) or fully through the vessel wall. Once the anchor 174 has been pushed into or through the vessel wall, a clinician then may exert a proximal pulling force on the pusher member 90 or the elongated flexible member 172, thereby causing the anchor head 180 to engage with the vessel wall and collapse or coapt the lumen of the vessel.

Additionally, or alternatively, the pusher member 90 may be configured to supply a sideways displacement force along the longitudinal axis of the anchor head 174 (e.g., radially within the vessel). For example, the anchor head 174 may be connected to the elongated flexible member 172 at an attachment point 178 such that the attachment point 178 remains relatively inflexible and the anchor head 180 remains generally perpendicular to the elongated flexible member 172. The pusher member 90 may engage the elongated flexible member 172 at the attachment point 178 to provide a lateral driving force enabling the anchor head 180 to be at least partially introduced into the vessel wall.

In some examples, the pusher member 90 may include one or more marker bands 92. The marker bands 92 may be visible bands applied to the pusher member 90 at spaced intervals, and may serve as a guide for a clinician to determine the positioning of the pusher member 90 or one or more of the anchors 174 within the vessel. For example, pusher member 90 may include a portion that remains outside the patient's body that includes marker bands 92. The clinician may then use the marker bands 92 as guidemarks to determine how far the vessel closure device 170 has been delivered into or retracted from the body of a patient. Additionally, or alternatively, the marker bands 90 may be used to assist the clinician in determining how much force need be applied to deliver the anchor 174 through the vessel wall or cause the vessel wall to collapse. For example, the distance between the one or more marker bands 92 may be approximately equal to the diameter of the target vessel, such that once anchor 174 has been introduced partially or entirely through a vessel wall, the proximal movement of the pusher member 90 by a distance equal to the space between two marker bands 92 may be sufficient to cause collapse or coaptation of the target vessel.

In some examples in which the vessel closure device includes multiple anchors, such as the examples of FIGS. 7 and 8 discussed below, the space between the adjacent marker bands 92 may represent a distance between adjacent anchors. The adjacent marker bands 92 may be used to assist the clinician to reposition the pusher member 90 so that a different anchor heads may be engaged to assist with the delivery or retraction of the vessel closure device.

The marker bands 92 may be formed using any suitable material or technique. In some examples, the marker bands 92 may be a printed or other visual mark on the pusher member 90 to provide a contrasting visual change along the pusher member 90. Additionally, or alternatively, marker bands 92 may include a physical change in the pusher member 90 such as a ring of material, a notch or raised bump or other protrusion in the pusher member 90 itself, or the like.

In some examples, the marker bands 92 may be distributed along a portion of the pusher member 90 that is introduced into the patient's body. In such examples, the marker bands 92 may include a radiopaque material, an echogenic material, or the like to enable a clinician to visually track the movement of pusher member 90 using, for example, an ultrasound probe or a fluoroscopy device from outside the patient's body.

Figure 5:
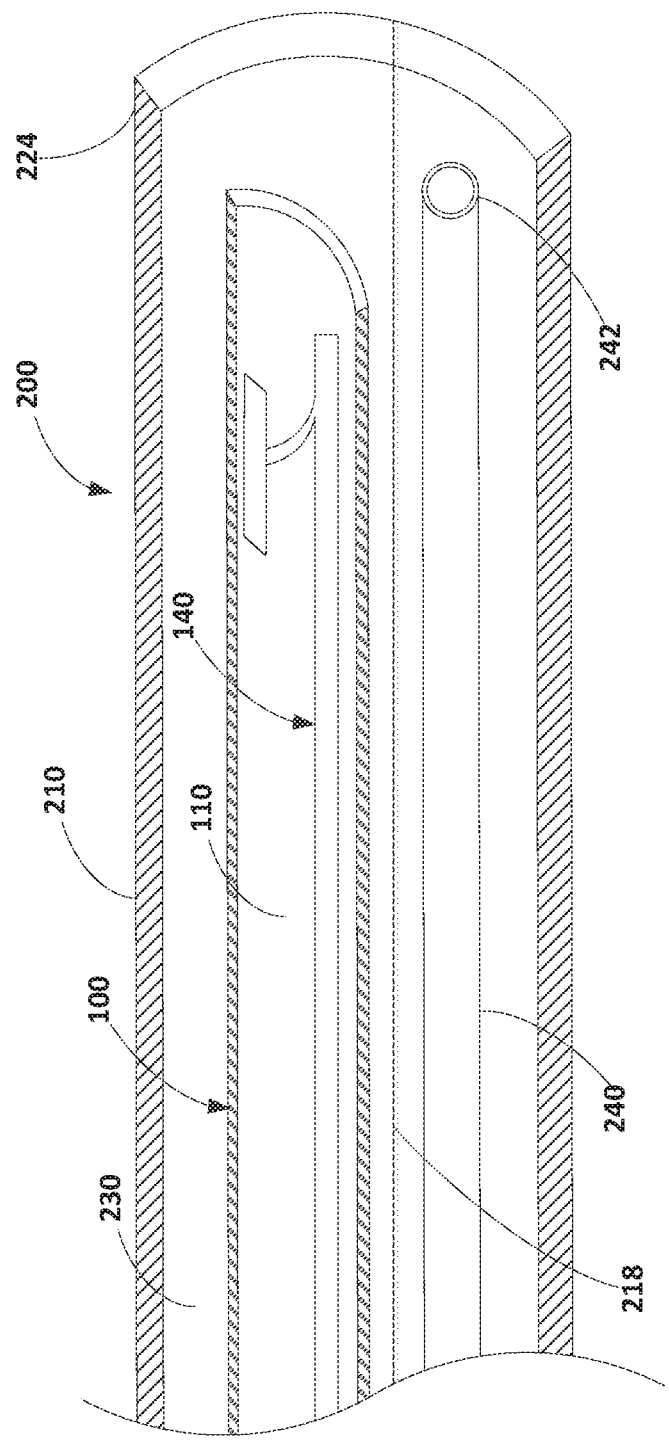
FIG. 5 is a cross-sectional view of another example vessel closure system, including a vessel closure device received within the lumen of a needle and an adhesive-delivery catheter, the needle and adhesive-delivery catheter are both received within the lumen of a delivery catheter, where the cross-section is taken along a longitudinal axis of the delivery catheter.

Referring now to FIG. 5, a cross-sectional view of an example vessel closure system 200 taken along a longitudinal axis 218 of a delivery catheter 210 is shown. The vessel closure system 200 may be used to deliver any of the vessel closure devices describe herein. As shown in FIG. 5, the vessel closure system 200 includes the needle 100 and the vessel closure device 140 of FIG. 3 within the delivery catheter 210. In FIG. 5, the needle 100 and the vessel closure device 140 are both received within a lumen 230 of the delivery catheter 210. In some examples, the vessel closure system 200 may also include devices to provide other adjunct therapies, such as an adhesive-delivery catheter 240 received within the lumen 230 of the delivery catheter 210. In some examples, the adhesive-delivery catheter 240 may be used to deliver an adhesive to a treatment site, whereas in other examples, adhesive-delivery catheter may be replaced with a catheter to be used to deliver other treatment materials to the treatment site, such as a sclerosing agent or other substance, or a device to deliver other treatment options, such as coils.

The delivery catheter 210 may be a flexible catheter configured to be advanced through the vasculature of a patient to a treatment site within a target vessel. The delivery catheter 210 may be made of any suitably flexible, biocompatible material, such as nylon, polyethylene terephthalate (PET), polyether block amide (PEBA), or others. In some examples, one or more portions of the delivery catheter 210 may include a radiopaque material, such as platinum, an alloy thereof, or other suitable radiopaque materials. The radiopaque material may enable a clinician to monitor the progress of the delivery catheter 210 through the vasculature and guide the delivery catheter 210 to a treatment site within the target vessel.

The dimensions and degree of flexibility of the delivery catheter 210 may be selected based on the location of the target vessel. For example, target vessels located within the cranium may require relatively smaller, more flexible catheters capable of being passed through the tortuous cranial vasculature than examples in which the target vessel is located within a vessel of the leg. Regardless of the location of the target vessel, the delivery catheter 210 may be dimensioned to receive the needle 100 and the adhesive-delivery catheter 240.

In the illustrated example, both the needle 100 and the adhesive-delivery catheter 240 may be received within a single lumen 230 of the delivery catheter 210. In other examples (not shown) the delivery catheter 210 may be a multi-lumen catheter, in which the needle 100 is received within one lumen and the adhesive-delivery catheter 210 is received within another lumen of the delivery catheter 210. Additionally, or alternatively, the adhesive-delivery catheter 240 may be constructed integrally with the delivery catheter 210. For example, a second lumen within the delivery catheter 210 may be dedicated to the delivery of a treatment materials such as an adhesive or sclerosing agent.

The delivery catheter 210 includes a distal end 224 past which the needle 100 and the adhesive-delivery catheter 240 may be extended during a procedure to the deliver the vessel closure device 140 within a target vessel to a treatment site. During placement of the vessel closure device 140, the delivery catheter 210 may be withdrawn proximally from the treatment site within the target vessel, but may remain in the target vessel until delivery of the vessel closure device 140 is completed. Upon completion of the procedure, the needle 100 and the adhesive-delivery catheter 240 may be withdrawn proximally back into delivery catheter 210. The vessel closure system 200 then may be withdrawn from the body with the needle 100 and the adhesive-delivery catheter 240 received within the lumen 230 of the delivery catheter 210.

In some examples, the delivery catheter 210 may aid in the advancement of the vessel closure device 140 to a target treatment site. For example, in examples where the vessel closure device 140 is delivered via the needle 100, the delivery catheter 210 may provide protection to the vessel wall of a patient by preventing the end 114 of the needle 100 from contacting the vessel wall as the vessel closure system 200 is navigated to a target treatment site.

Figure 6:
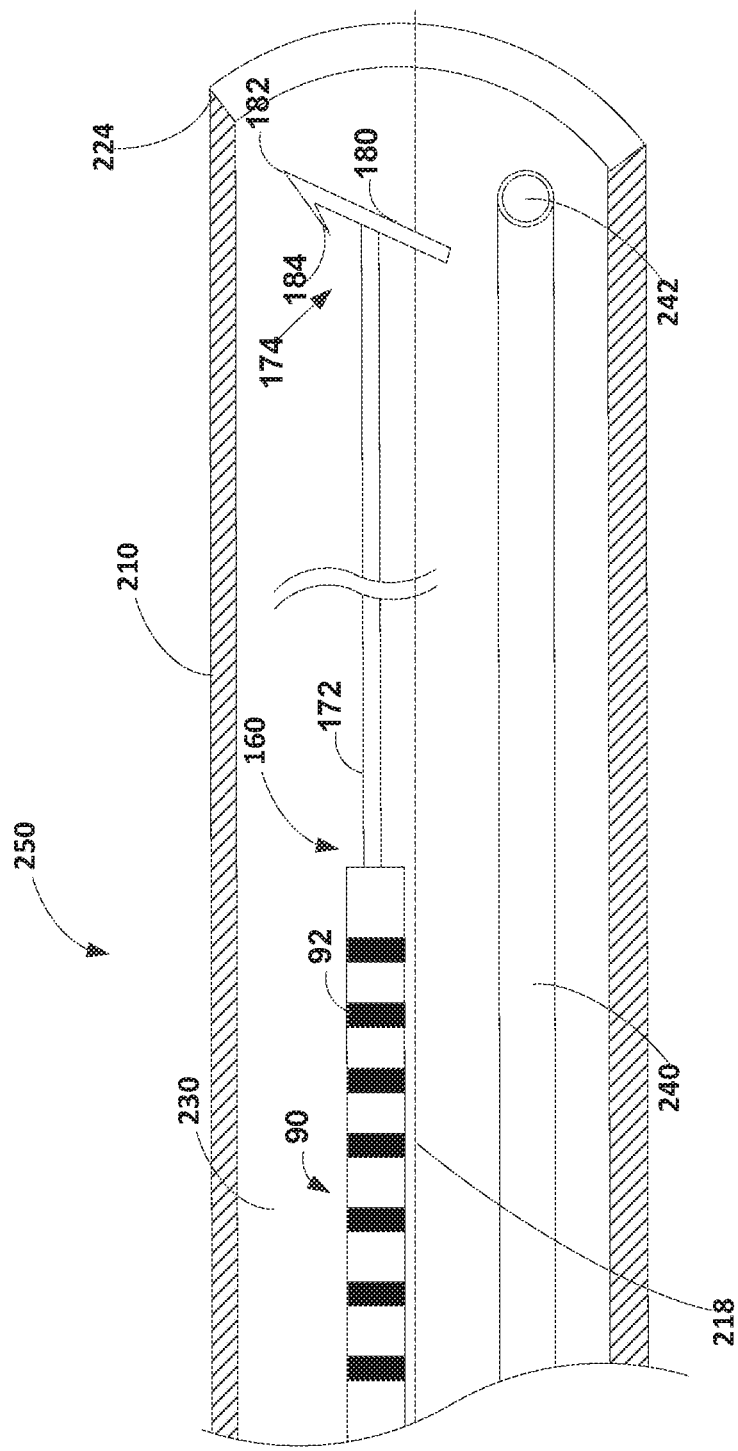
FIG. 6 is a cross-sectional view of another example vessel closure system, including the vessel closure system of FIG. 4 and an adhesive-delivery catheter, both received within the lumen of a delivery catheter, where the cross-section is taken along a longitudinal axis of the delivery catheter.
Figure 8:
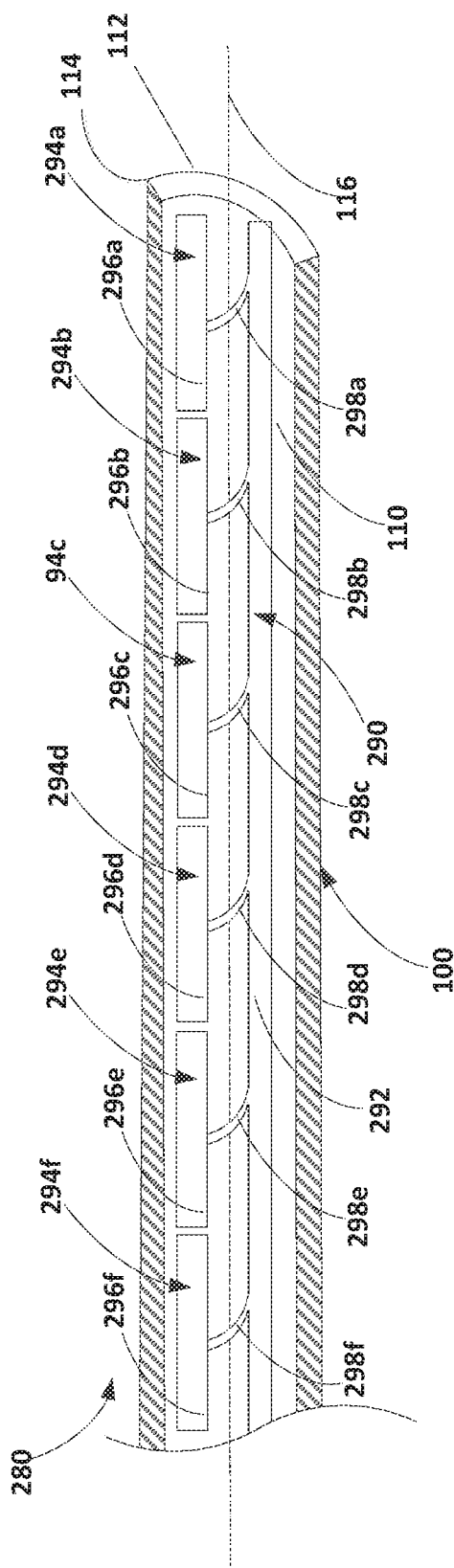
FIG. 8 is a side view of an example vessel closure system including a needle and the vessel closure device of FIG. 7 received within a lumen of the needle, where the cross-section is taken along a longitudinal axis of the needle.
Figure 9:
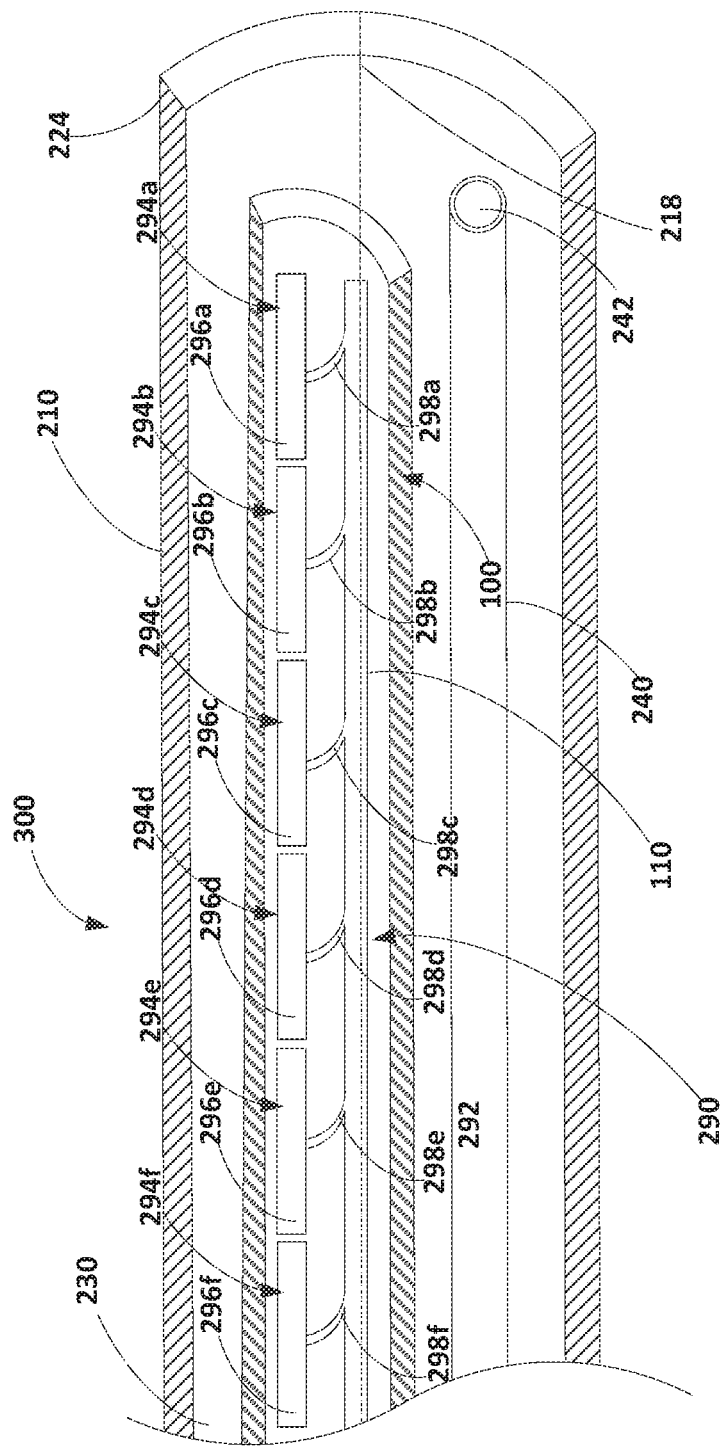
FIG. 9 is a cross-sectional view of another example vessel closure system, including the needle and vessel closure device of FIG. 8 along with an adhesive-delivery catheter received within the lumen of a delivery catheter, where the cross-section is taken along a longitudinal axis of the delivery catheter.

In some examples, the vessel closure system 200 may be configured to exclude the use of the needle 100. For example, FIG. 6 is a cross-sectional view of another example vessel closure system 250 that includes the adhesive-delivery catheter 240 and the vessel closure system 160 of FIG. 4 including the vessel closure device 170 and the pusher member 90, all received within the lumen 230 of the delivery catheter 210, where the cross-section is taken along the longitudinal axis 218 of the delivery catheter 210. The delivery catheter 210 may be used to transport the vessel closure device 170 to a treatment site where the pusher rod 90 is then used to deliver the anchor 174 through the vessel wall substantially as described above. The adhesive-delivery catheter 240 may then deliver a treatment material such as an adhesive or sclerosing agent via lumen 242 to the treatment site and the pusher member 90 or the elongate flexible member 172 may be pulled to engage the anchor head 180 with the vessel wall causing the lumen of the vessel to close and seal in conjunction with the treatment material. In some examples, the vessel closure devices described herein may include a plurality of anchors disposed along the length of the elongated flexible member. FIGS. 7-9 illustrate example vessel closure devices and vessel closure systems that each include a plurality of anchors. In such examples, the plurality of anchors may be delivered to a series of treatment sites along a length of the target vessel, thereby allowing the vessel to be sequentially closed over an extended length of the vessel. Such vessel closure device that includes a plurality of anchors may be advantageous in some cases, such as examples in which the anatomical features of the target vessel or other target bodily structure may render the treatment site resistant to closure or where it is desirable to close an extended length of the vessel.

Figure 7:
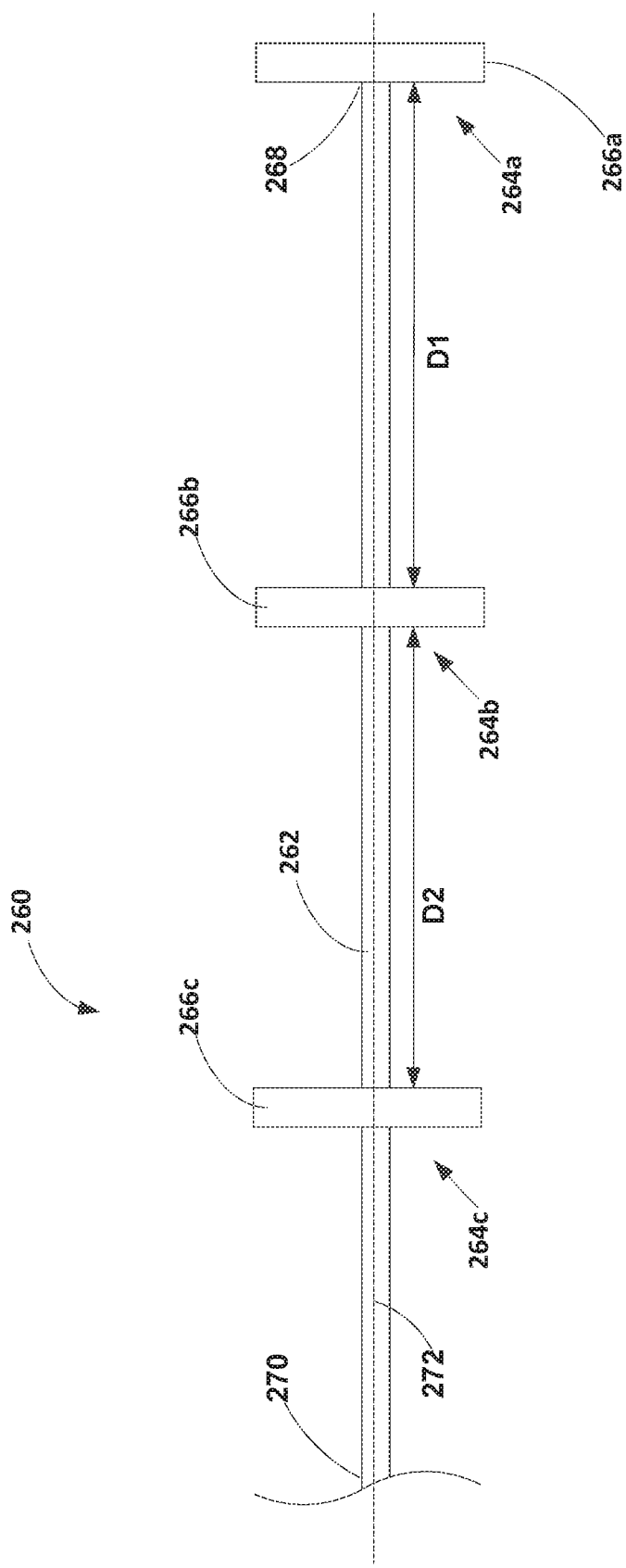
FIG. 7 is a side view of an example vessel closure device including an elongated flexible member and a plurality of anchors distributed along the elongated flexible member.

FIG. 7 is a side view of an example vessel closure device 260 that includes an elongated flexible member 262 and a plurality of anchors 264a-264c disposed along the length of the elongated flexible member 262, each of the anchors 264a-264c including the respective anchor heads 266a-266c. As shown in FIG. 7, the anchor heads 266a-266c may be attached directly to and extend from elongated flexible member 262 at a non-parallel angle relative to a longitudinal axis 272 of the elongated flexible member 262, such that the intersection of each the anchor heads 266a-266c with the elongated flexible member 262 defines a T-shape (as described above). The respective components of the vessel closure device 260 (e.g., the elongated flexible member 262, the anchors 264a-264c, optional anchor tethers, and the like) may be substantially similar to the various deceive components and features described above with respect to FIGS. 1-3 and will not be discussed again in detail here.

In some examples, the plurality of anchors 264a-264c may be distributed along the length of the elongated flexible member 262 at regular intervals (e.g., substantially equidistant from each other), beginning with a distal-most anchor head 266a near a distal end 268 of the vessel closure device 260 and ending with a proximal-most anchor head 266c at a more proximal position along the elongated flexible member 262. For example, distance D1 between the anchors 266a, 266b and distance D2 between anchors 266b, 266c may be equal, where distances D1 and D2 are measured along the longitudinal axis 272 of the elongated flexible member 262.

In other examples, the anchors 264a-264c may be distributed along the length of the elongated flexible member 260 at irregular intervals. For example, a distance D1 between the anchors 266a, 266b and a distance D2 between the anchors 266b, 266c may be different. As an example, one or more of the anchors 264a-264c that may be distributed near a distal end 270 of the elongated flexible member 260 may be distributed at smaller intervals than one or more of the anchors 264a-264c that may be distributed further away from the distal end 270 of the elongated flexible member 260.

The spacing between adjacent the anchors 264a-264c and quantity of the anchors 264a-264c may be dependent on a variety of factors including, for example, the diameter of the vessel to be closed, the longitudinal length of the vessel to be closed, the geometry of the vessel, and the like. In some cases, it may be advantageous for the distribution of the anchors 264a-264c along the elongated flexible member 262 to be concentrated within one or more regions of the elongated member 262. For example, a target vessel may include one or more portions, such as a vessel branch point, that may be resistant to closure. Thus, in such examples, distribution of a higher concentration of the anchors 264a-264c along the portion of the elongated flexible member 262 traversing the branch point, with one or more widely-spaced anchors of the anchors 264a-264c placed further from the branch point, may provide more secure closure of the vessel than examples in which the same number of the anchors 264a-264c are distributed at regular intervals.

In some examples, the anchors 264a-264c may be separated from each other at intervals equal to at least the diameter of the target vessel. In some examples, the anchors 264a-264c may be separated from one another along the elongated flexible member 262 by about 5 millimeters (mm) to about 30 mm, such as about 5 mm to about 10 mm, about 5 mm to about 20 mm, or about 10 mm to about 25 mm. In other examples the anchors 263a-264c may be separated by distances less than 5 mm or greater than 30 mm.

Vessel closure device 260 may be constructed using any of the materials describe above. For example, elongated flexible member 270, plurality of anchors 264a-264c, or both may include biocompatible materials including, for example, non-biodegradable materials, such as high-density polyethylene (HDPE), polyester, nitinol, stainless steel, or other suitable non-biodegradable materials. Additionally, or alternatively, elongated flexible member 270, plurality of anchors 264a-264c, or both may include biodegradable or bioabsorbable materials.

As with the vessel closure device 10 of FIG. 1, the vessel closure device 260 may be configured to be received within a lumen of one or more needles, such as the lumen 110 of the needle 100 of FIG. 4. In such examples, when the vessel closure device 260 is received in the lumen 110, each of the anchor heads 266a-266c may be folded or partially folded against the elongated flexible member 262 such that the longitudinal axis of the respective anchor heads 266a-266c, the longitudinal axis of the elongated flexible member 262, and the longitudinal axis of needle 100 at least partially align while vessel closure device 260 is within lumen 110 of the needle 100. During a procedure to place the anchors 264a-264c within a wall of the target vessel, a needle may be advanced through the vessel wall at multiple locations along a length of the target vessel, with one or more of the anchors 264a-264c being placed into the vessel wall at each location. A proximal pulling force may be applied to the elongated flexible member 262 following the placement of each of the anchor heads 266a-266c, thereby collapsing the target vessel in a plurality of locations that correspond to the placement site of the respective anchor head of the plurality of the anchor heads 266a-266c.

In some examples, each of the anchors 264a-264c may include a respective anchor tether substantially similar to the anchor tether 46 described above with respect to FIG. 2A. FIG. 8 is a cross-sectional view of an example vessel closure system 280 that includes the needle 100 and a vessel closure device 290 received within the lumen 110 of the needle 100, where the cross-section is taken along the longitudinal axis 116 of the needle 100. The vessel closure device 290 includes an elongated flexible member 292 and a plurality of anchors 294a-294f distributed along a portion of the flexible member 292. The plurality of anchors 294a-294f may include respective anchor heads 296a-296f and anchor tethers 298a-298f connecting the respective anchor heads 296a-296f to the elongated flexible member 292. Each of the anchor heads 296a-296f may include one or more of the structural features (e.g., barbs, sharp ends, or the like) as described above with respect to FIGS. 1-3.

As with the vessel closure device 260 of FIG. 7, the anchors 294a-294f may be distributed along the length of the elongated flexible member 292 at regular intervals in some examples, and at irregular intervals in other examples. The advantages and features of the distribution of the anchors 294a-294f along the elongated flexible member 292 may be substantially similar to those described above with respect to the vessel closure device 260 and will not be discussed again in detail here.

In some examples, the alignment of the anchor heads 296a-296f along the elongated flexible member 292 may assist with the delivery of the anchors heads 296a-296f out from the lumen 110 of the needle 100 and into the vessel wall of the target vessel. For example, a distal pushing force may be applied to the proximal most anchor head 296f (e.g., via a pusher member or the like). The distal pushing force may be distributed in a proximal-to-distal direction. Each anchor head of the anchor heads 296a-296a may contact an adjacent anchor head such that each anchor head of anchor heads 296a-296f may help drive the distally-next anchor head out from the lumen 110 of the needle 100 and into the vessel wall.

FIG. 9 is a cross-sectional view of another example vessel closure system 300, which may include the needle 100, the vessel closure device 290, and the adhesive-delivery catheter 240, where the cross-section is taken along the longitudinal axis 218 of the delivery catheter 210. In FIG. 9, both the vessel closure device 290 and the adhesive-delivery catheter 240 are shown received within the lumen 230 of the delivery catheter 210. One or more features of the vessel closure system 300 may be substantially similar to the components and descriptions of the vessel closure systems 90, 160, 200, 250, and 280 described with respect to any of the previous vessel closure devices or systems described herein.

Figure 10:
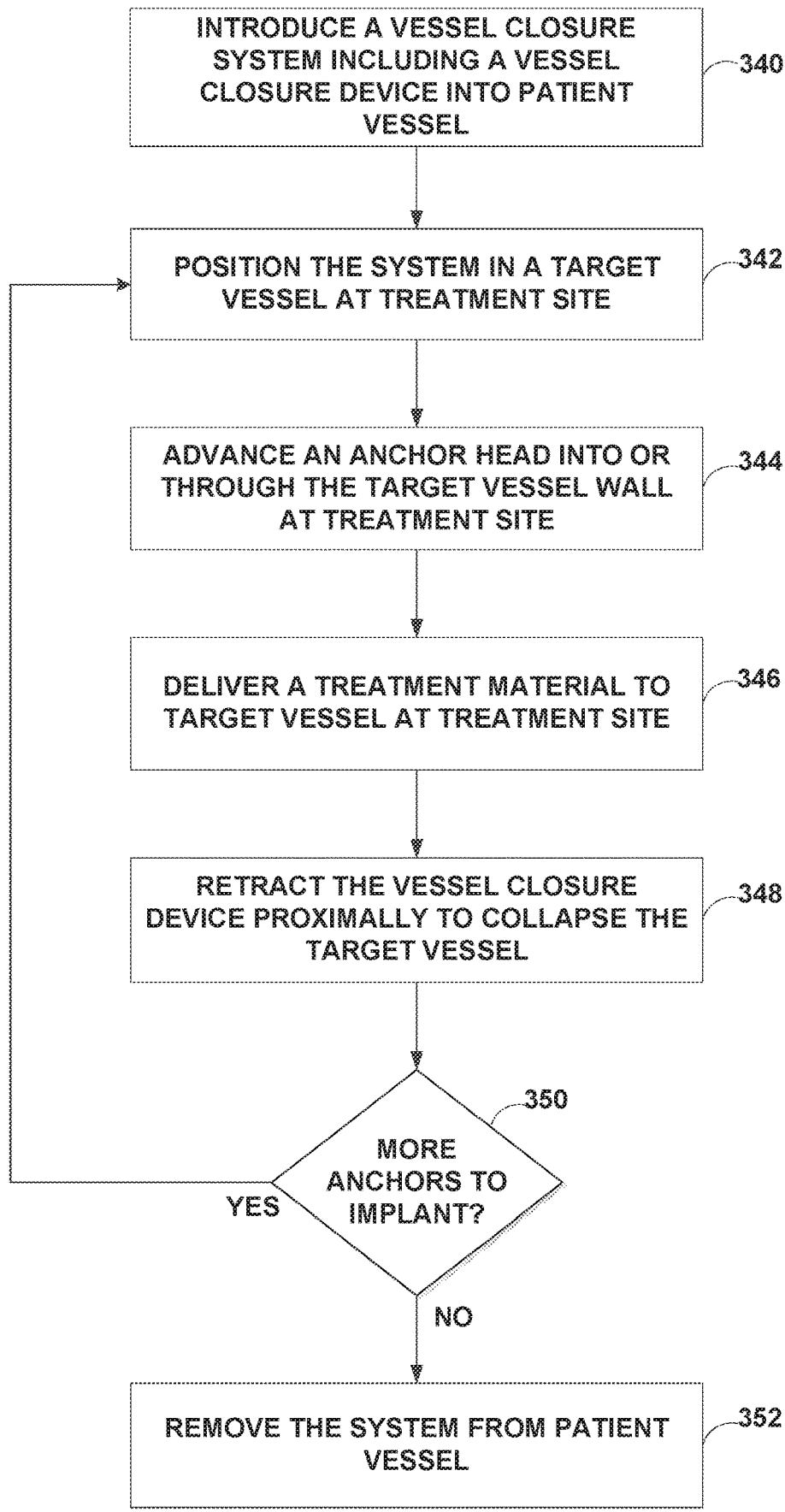
FIG. 10 is a flow diagram illustrating an example method of using a vessel closure device or vessel closure system as described herein.

FIG. 10 is a flow diagram illustrating example technique that may be implemented by a clinician to deploy and use a vessel closure system as described herein. The flow diagram of FIG. 10 is described in conjunction with FIGS. 11A-11F which illustrate a series of cross-sectional views showing the vessel closure system 300 being operated within a vessel 320 of a patient. While FIG. 10 is described in context with the vessel treatment system of FIGS. 11A-11F, the techniques of FIG. 10 may be used in conjunction with other techniques, other vessel closure devices (e.g., the vessel closure devices of FIGS. 1-8) or other vessel closure systems (e.g., the vessel closure systems of FIGS. 3-5, 8, and 9).

Additionally, or alternatively, the vessel closure system of FIGS. 11A-11F may be used in conjunction with other techniques or with other vessel closure devices (e.g., the vessel closure devices of FIGS. 1-8).

Figure 11C:
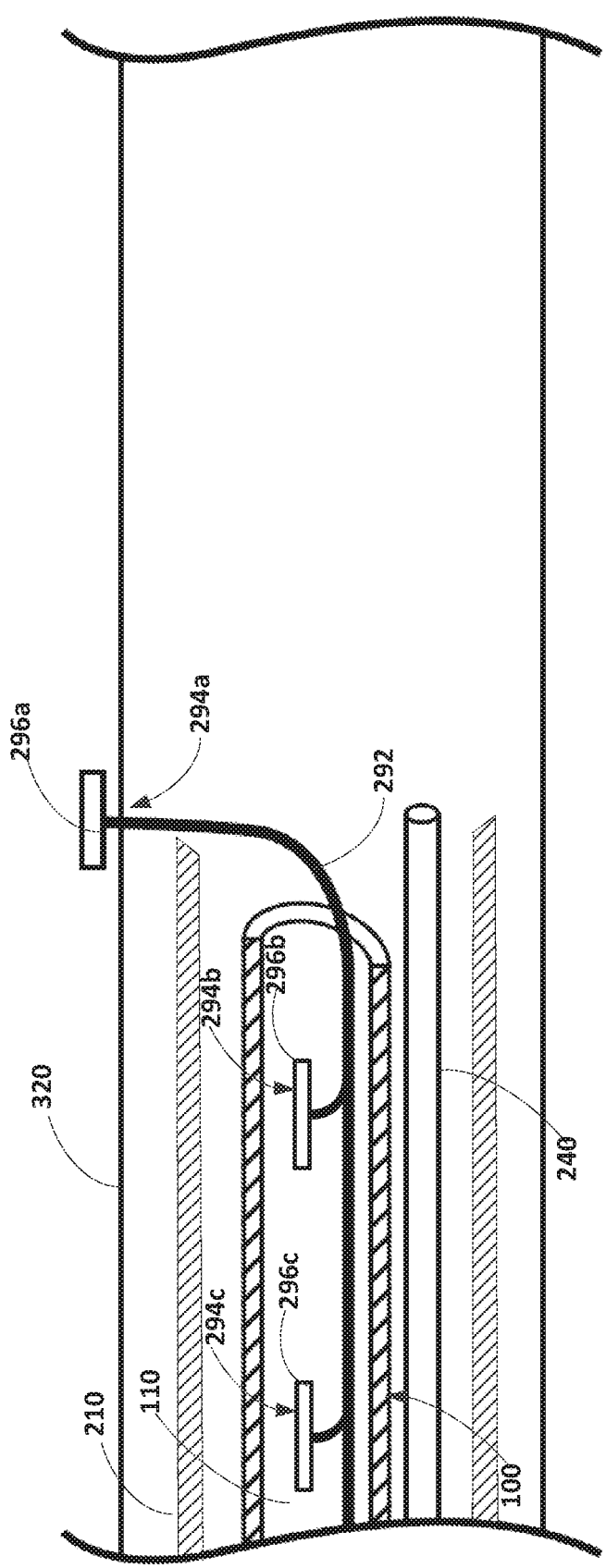

The technique of FIG. 10 includes introducing the vessel closure system 300 into the vessel 320 of a patient (340). As shown in FIG. 11A, vessel closure system 300 may include the needle 100 and the adhesive-delivery catheter 240 configured to be received within the lumen 230 of the delivery catheter 210. In FIG. 11A, the vessel closure device 290 is disposed within the lumen 110 of the needle 100. The vessel closure device 290 may include the elongated flexible member 292 and the plurality of anchors 294a-294f. The plurality of anchors 294a-294f may include respective the anchor heads 296a-296f and the optional anchor tethers 298a-298f, as described above with respect to FIG. 8. As shown in FIG. 11A, the anchors 294a-294f including the anchor tethers 298a-298f and the anchor heads 296a-296f are shown collapsed under the biasing force of the needle 100 into a radially compressed configuration. Each of the respective components of the vessel closure system 300 may be substantially as described above with respect to FIGS. 8 and 9. Although the operation of the vessel closure system 300 of FIGS. 11A-11F is depicted as including a single needle 100, it should be understood that the steps described with respect to FIGS. 11A-11F are equally applicable to example vessel closure systems that include more than one needle 100, or may include more than one vessel closure device 290. For example, any of the steps described below may also be performed with one or more additional needles 100 or vessel closure devices 290, either simultaneously or sequentially.

In some examples, the vessel closure system 300 may be introduced into a target vessel 320 of a patient at a location relatively far from a treatment site. The location relatively far from the treatment site may either be upstream from the treatment site within the target vessel 320 or downstream of the treatment site. In other examples, the vessel closure system 300 may be introduced at a location relatively near the treatment site. In all examples, one or more components of the vessel closure system 300 may be sized to accommodate the dimensions of the point of entry into which the vessel closure system 300 is introduced, as well as the dimensions of the vessel 320 containing the treatment site. In some examples, to track the relative position of the delivery catheter 210, the catheter may include one or more radiopaque portions, which may enable the clinician to monitor the progress of the delivery catheter 210 through the vasculature of the patient and guide the delivery catheter 210 to one or more treatment sites within the target vessel 320 using a medical imaging device.

Upon introduction of the vessel closure system 300 into the vessel of the patient (e.g., a patient's vasculature) (340), the distal end of the vessel closure system 300 may be positioned adjacent to a first target treatment site within the vessel 320 (342). The clinician may then advance a first anchor 294a entirely or partially through the wall of the target vessel 320 (344). For example, as shown in FIG. 11B the delivery catheter 210 may be advanced by a clinician through the vasculature of a patient to a first target treatment site 360 within the target vessel 320. Once at the first target treatment site 360, a first anchor 294a may be advance entirely though the vessel wall using, for example, the delivery needle 100 to pass the first anchor 294a through the vessel wall.

As shown in FIG. 11B, the distal end 112 of the needle 100 is shown extending toward and puncturing the wall of the target vessel 320, with the first anchor 294a being expelled from the needle 100 and delivered through the puncture created by the needle 100. After the first anchor 294a is delivered through the puncture created by the needle 100, and the needle 100 is retracted, the wall of the target vessel 320 may close back around a portion of the first anchor 294a, such as a first anchor tether 298a of the first anchor 294a. In examples in which the first anchor 294a is delivered completely through the wall of the target vessel 320, the anchor head 296a of the first anchor 294a may rest against an outer surface of the wall of the target vessel 320 once the puncture created by the needle 100 closes around the first anchor 294a. The length of anchor head 296a may be greater than the diameter of needle 100 so as to prevent the anchor head from being pulled back through the puncture site. In examples in which the first anchor 294a is delivered partially through the wall of the target vessel 320, the first anchor 294a may be embedded within, for example, the media layer of the target vessel 320 and the portion of the wall punctured by the needle 100 closes around the first anchor 294a once the needle 100 is removed.

In some examples, a vessel closure system 300 may be configured to include more than one needle 100. Each needle may be configured to deliver a respective anchor 294a-294f of vessel closure device 290, or each needle may be configured to include a different vessel closure device 290. For example, two of the needles 100 may be included in the vessel closure system 300. The inclusion of more than one needle may allow a clinician more easily coapt the target vessel 320, such as examples in which the target vessel 320 has relatively large dimensions. In some such examples, the delivery catheter 210 may be sized to accommodate the two needles. Each of the needles 100 may be configured to receive a vessel closure device 290 within the lumen 110 of the needle 100.

In some examples, the needle 100 may be curved away from the longitudinal axis 218 of the delivery catheter 210 and toward the wall of the target vessel 320. For example, the needle 100 may be constructed using a heat-set shape-memory material to introduce a curvature to the needle 100. The curvature of the distal end 112 of the needle 100, as illustrated in FIG. 11B, may aid the clinician in steering the sharp point 114 at distal end 112 of needle 100 through the wall of target vessel 320. Upon extension of the needle 100 past the distal end 224 of the delivery catheter 210 at least the distal end 112 of the needle 100 may assume the curved shape illustrated in FIG. 11B. In examples in which a vessel closure system includes more than one of the needle 100, (e.g., two needles 100), the needles 100 may be independently advanced through the vessel wall at the first target treatment site 360. For example, one of the needles 100 may be configured to curve toward a first portion of the wall of the target vessel 320, and a second needle may be configured to curve toward a second portion wall of the target vessel 320 that is radially offset from the first portion of the wall of the target vessel 320. In some examples, the needles 100 may be configured to curve in substantially opposite directions from one another.

Once the delivery needle 100 has passed through the vessel wall, the first anchor 294a may be ejected from the needle lumen 110, and the needle 100 withdrawn from the vessel wall, leaving the first anchor 294a on the exterior of the target vessel 320 at a first treatment site 360 (e.g., FIG. 11C). In some examples where vessel closure device 290 includes a plurality of anchors 294a-294f, the technique shown in FIG. 10 may include delivering more than one of the anchors 294a-294f to the first treatment site 360. For example, a second anchor (e.g., anchor 294b) may be delivered to a different positions about the circumference of the target vessel 320 relative to the first anchor 294a (e.g., about 180 degrees relative to first anchor 294a). In some such examples, the first anchor 294a and the second anchor 294b may both be attached to or integral with the elongated flexible member 292 of the vessel closure device 290, and optionally may be configured to extend away from the elongated flexible member 292 in substantially opposite directions from one another. In such examples, both the first anchor 294a and the second anchor 294b may be inserted partially or completely through the vessel wall at the first treatment site 360 and the portion of the elongated flexible member 292 connecting the first and second anchors 294a, 294b may be pulled to engage the two anchors with the vessel wall to cause the target vessel 320 to coapt at the first treatment site 360. Additionally, or alternatively, the first anchor 294a and additional anchor to be delivered to the first target treatment site 360 may be attached to or integral with separate elongated flexible members of separate vessel closure devices. Once the two anchors have been delivered, the two vessel closure devices may be independently pulled to cause the target vessel 320 to coapt at the first treatment site 360. In some examples in which more than one anchor (e.g., two or more of anchors 294a-294f) is delivered to the first treatment site 360, the anchors may be delivered through the vessel wall using the same or separate needles 100.

Optionally, prior to or after the first anchor 294a of the vessel closure device 290 is advanced through the wall of the target vessel 320 (344) at the first treatment site 360, a first aliquot of treatment material 370, such as an adhesive (e.g., cyanoacrylate or other biocompatible adhesive) or sclerosing agent may be delivered through the lumen 242 of the adhesive-catheter 240 to the first treatment site 360 adjacent the first anchor 294a (346).

Figure 11D:
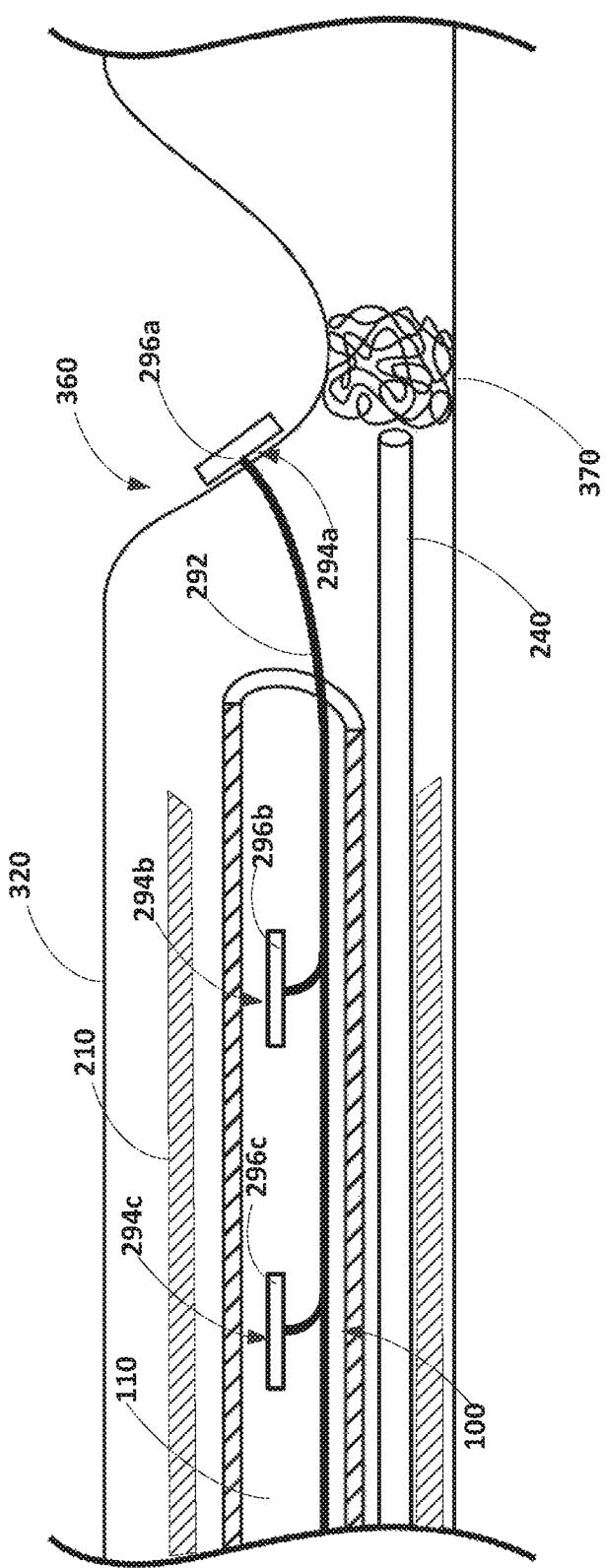

Next, the clinician retracts the vessel closure device 290 proximally to collapse or coapt the target vessel (348). For example, the clinician may apply a proximal pulling force to a proximal portion of the vessel closure device 290 to collapse the target vessel 320 (348) at the first treatment site 360. FIG. 11D illustrates a proximal pulling force being exerted upon the elongated flexible member 292 of the vessel closure device 290, causing the lumen of the target vessel 320 to collapse radially inward. In some examples, the proximal pulling force may be applied on a proximal portion of the vessel closure device 290, such as a proximal portion of the elongated flexible member 292, or a pusher member where such a device is used. The proximal pulling force is transferred along the elongated flexible member 292 to the first anchor head 296a, which in turn transfers the force to the outer wall of the target vessel 320. The force exerted by first the anchor head 296a on the outer wall of the target vessel 320 causes the target vessel 320 to move radially inward from the first anchor head 296a and contact the first aliquot of treatment material 370 at the first treatment site 360, thereby closing the target vessel 320 at the first treatment site 360. The elongated flexible member 292 may be held in this position for a sufficient duration to let first the aliquot of treatment material 370 to work. In examples in which a vessel closure system 300 includes more than one vessel closure devices 290 that are used to collapse the first target treatment site 360 at opposing or radially-offset portions of the target vessel 320, the clinician may retract and hold the elongated flexible members 292 of each of the vessel closure devices 290 for a sufficient duration to let the first aliquot of treatment material to work. Once the first aliquot of treatment material 370 has worked (e.g., cured or caused sclerosis), the clinician may optionally clip the elongated flexible member 292 to a desired length.

Figure 11E:
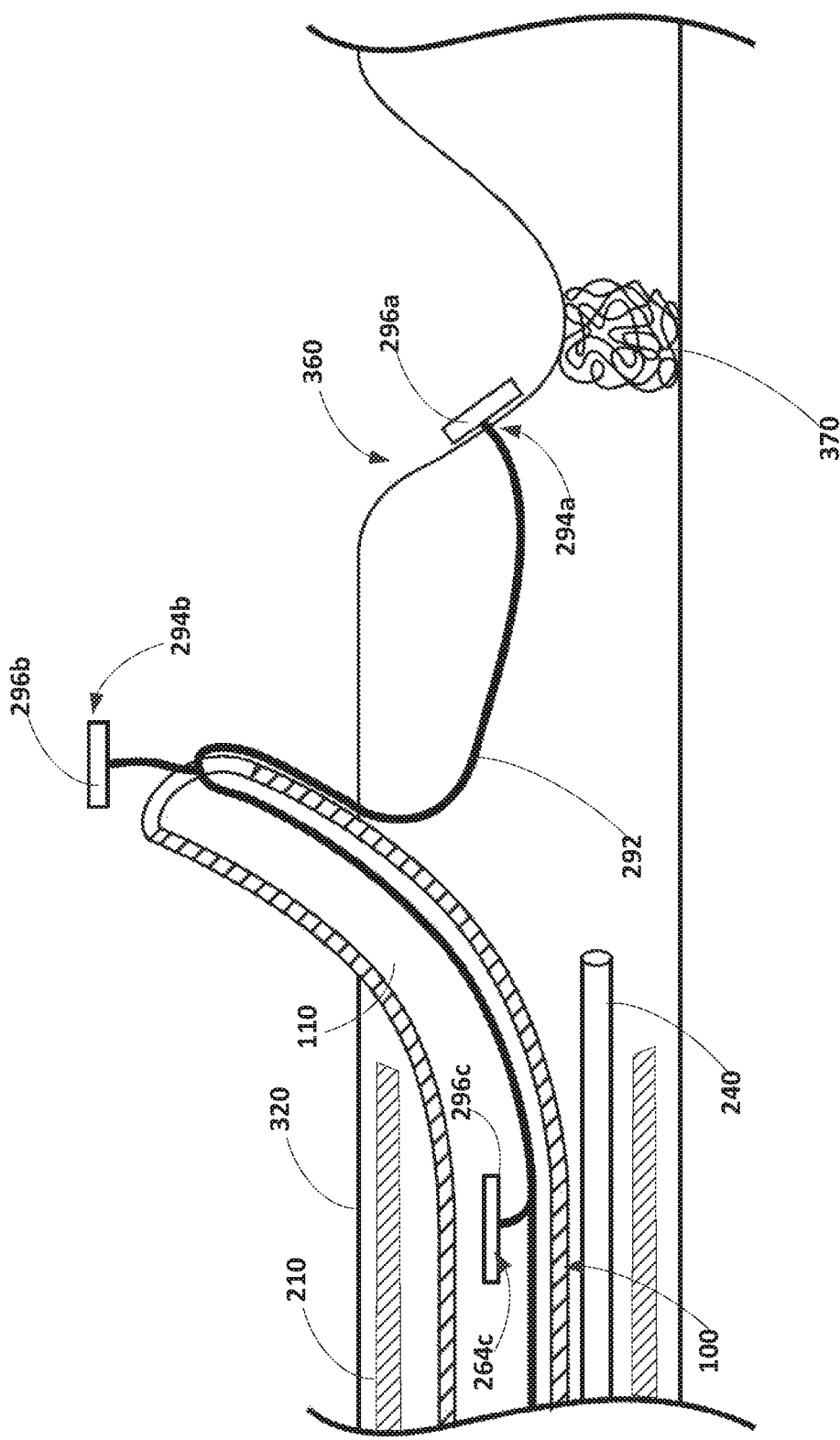

In examples in which an example vessel closure device used with the vessel closure system 300 includes a plurality of anchors, such as the anchors 294a-294f of the vessel closure device 290, the technique shown in FIG. 10 may include determining whether there are additional anchors to implant (350) at one or more additional treatment sites within the target vessel 320. In response to determining there are additional anchors to implant at one or more additional treatment sites ("Yes" branch of block 350), the clinician may repeat the preceding steps to deliver one or more additional anchors 294b-294f to one or more additional treatment sites within vessel 320. For example, FIG. 11E illustrates the placement of a second anchor of the vessel closure device 290 (e.g., anchor 294b if only the first anchor 294a is delivered at the first treatment site 360, or others of the remaining anchors 294c-294f if multiple anchors are delivered at the first treatment site 360), through the wall of the vessel 320 at a second treatment site 362. The second anchor 294b may be deployed through the vessel wall using substantially the same techniques as described above with respect to the first anchor 294a.

For example, once the vessel 320 has been collapsed or coapted at the first treatment site 360, the needle 100 may be withdrawn proximally of the first anchor 294a and pierced through the vessel wall at the second treatment site 362. In some such examples, the elongated flexible member 292 may substantially follow the path created by the needle 100. As shown in FIG. 11E, for example, the elongated flexible member 292 extends proximally from the previously-deployed first anchor 294a tracking up an outer surface of the needle 100, and into the lumen 110 of the needle 100. A second anchor tether 298b, which has been advanced distally past the needle 100 and freed from the biasing force of the needle 100, is shown extending away from the elongated flexible member 292 during the deployment of the second anchor 294b. Additionally, or alternatively, the act of passing the needle through the vessel wall at the second treatment site 362 may cause the elongated flexible member 292 to sever. In such examples, because the second anchor 294b will still reside within the lumen 110 of the needle 100, the subsequent deployment of the second anchor 294b will not be affected by the separation of the first anchor 294a from the elongated flexible member 292.

Figure 11F:
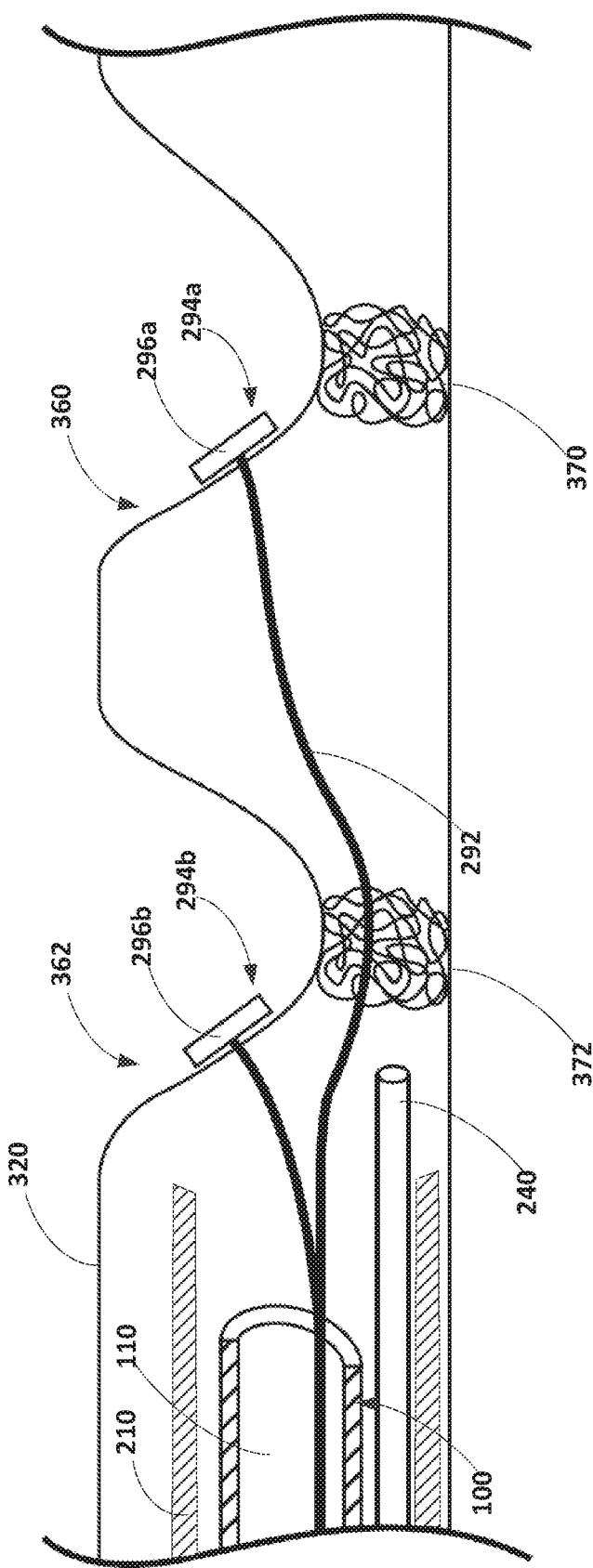

As shown in FIG. 11F, once the second anchor 294b is advanced through second treatment site, the needle 100 can be withdrawn back through the vessel wall. A proximal pulling force may then be exerted upon the elongated flexible member 292, causing the wall of the target vessel 320 to collapse radially inward at the second treatment site 362 as a second aliquot of treatment material 372, such as an adhesive (e.g., cyanoacrylate or other biocompatible adhesive) or sclerosing agent is delivered via the adhesive-delivery catheter 240 to the second treatment site 362. The proximal pulling force is transferred along the elongated member 292 to the second anchor head 296b, which in turn transfers the force to the outer wall of the target vessel 320. The force exerted by the second anchor head 296b on the outer wall of the target vessel 320 causes the target vessel 320 to move radially inward from the second anchor head 296b and contact the second aliquot of treatment material 372 at the second treatment site 362, thereby closing the target vessel 320. The force on the elongated flexible member 292 may be maintained to enable the second aliquot of treatment material 372 to cure. The entire process can then be repeated as many times as necessary to close target vessel along a target length of the vessel. While the second treatment site 362 is shown as being on the same side of the vessel 320 as the first treatment site 360, it should be understood that the second treatment site 362 may be located radially offset from the first treatment site 360, such as by 90° or 180° around the vessel 320. By radially offsetting the second treatment site 362, the second anchor 294b may continue to more effectively provide the proximal pulling force on the elongate flexible member 292 and thus the first anchor 294a. In some such examples, the second treatment site 362 may be positioned at substantially the same longitudinal position along a length of the vessel 320 as the first treatment site 360. In other such examples, the second treatment site 362 may be positioned distally or proximally of the first treatment site 360.

In response to determining there are no additional anchors to implant ("NO" branch of block 350), the clinician may withdraw the needle 100, the adhesive-delivery catheter 240, and/or any other system components into the delivery catheter 210 and the vessel closure system 300 may be removed from the vasculature of the patient (352) leaving behind at least portions of vessel closure device 290.

Although the example treatment procedures of FIGS. 11A-11F are described as being carried out with particular examples of the vessel closure devices and vessel closure systems described herein, other example vessel closure devices and systems may be used at any step of the procedure. For example, the steps illustrated in FIGS. 11A-11D may be carried out using vessel closure device 70 of FIG. 2B and the vessel closure system 160 of FIG. 6, or any other single-anchor system described herein. In another example, the steps illustrated in FIGS. 11A-11F may be carried out using any example vessel closure device or systems that include a plurality of anchors.

Various aspects of the disclosure have been described. These and other aspects are within the scope of the following claims.

What is claimed is:

1. A vessel closure system comprising:
   a catheter configured to be introduced into a vessel of a patient, the catheter defining a catheter lumen; and
   a vessel closure device configured to be received within the catheter lumen, the closure device comprising:
      an elongated flexible member; and
      a plurality of anchors attached to the elongated flexible member, the anchors of the plurality of anchors being distributed along a length of the elongated flexible member, wherein each anchor is fixably attached to the elongated flexible member to maintain a pre-determined interval from an adjacent anchor, and wherein each anchor comprises an anchor head configured to be introduced into a wall of the vessel and engage with the wall of the vessel to cause the wall to move radially inward in response to a proximal pulling force applied to the elongated flexible member.

2. The system of claim 1, wherein each anchor head is configured to engage with the wall of the vessel at one attachment point to cause the vessel wall to move in response to a proximal pulling force applied to the elongated flexible member while the anchor head is engaged with the vessel wall at only the one attachment point.

3. The system of claim 1, wherein each anchor head is configured to be introduced entirely through the wall of the vessel.

4. The system of claim 1, wherein at least one anchor head has a first end and a second end opposite the first end, the first end and the second end of the anchor head being configured to be introduced through the wall of the vessel.

5. The system of claim 1, wherein at least one anchor head has a first end and a second end opposite the first end, at least one of the first end or the second end of the anchor head defining a sharp point configured to pierce through the wall of the vessel.

6. The system of claim 5, wherein at least one anchor head further comprises a barb.

7. The system of claim 1, wherein each anchor of the plurality of anchors further comprises an anchor tether mechanically connected to the respective anchor head, the anchor tether extending at a non-parallel angle relative to a longitudinal axis of the anchor head.

8. The system of claim 1, wherein each anchor of the plurality of anchors is collapsible toward the elongated flexible member under a biasing force.

9. The system of claim 1, wherein each anchor head has a greater cross-sectional dimension than the elongated flexible member, the cross-sections being taken perpendicular to respective longitudinal axes of the anchor head and elongated flexible member.

10. The system of claim 1, wherein at least one of the elongated flexible member or the plurality of anchors is configured to biodegrade within the patient or to be bioabsorbable by the patient.

11. The system of claim 10, wherein each anchor of the plurality of anchors comprises one of polylactic acid (PLLA), poly(lactic-co-glycolic) acid (PLGA), or a polysaccharide.

12. The system of claim 1, wherein each anchor of the plurality of anchors comprises at least one of high-density polyethylene (HDPE), polyester, nitinol, or stainless steel.

13. The system of claim 1, wherein each anchor of the plurality of anchors comprises an echogenic or radiopaque material.

14. The system of claim 1, further comprising a sclerosing agent on at least one anchor head of the plurality of anchors.

15. The system of claim 1, further comprising a needle configured to be received within the catheter lumen, the needle defining a needle lumen configured to receive at least a part of the vessel closure device and deliver the anchor head of at least one anchor of the plurality of anchors through the vessel wall.

16. The system of claim 15, wherein the needle defines a curved distal portion configured to extend away from the catheter when the needle exits the catheter lumen.

17. The system of claim 15, wherein the anchor head has a smaller cross-sectional dimension than the needle lumen, the cross-section being taken in a direction perpendicular to a longitudinal axis of the anchor head.

18. The system of claim 15, wherein the needle lumen is sized to receive all of the anchors of the vessel closure device.

19. The system of claim 1, further comprising a pusher member configured to be received within the catheter lumen and apply a force to at least one of the anchors of the plurality of anchors to push the anchor head into the vessel wall.

20. The system of claim 1, wherein the catheter comprises a first catheter, the system further comprising a second catheter configured to deliver a treatment material to a location within the vessel adjacent at least one anchor of the plurality of anchors, the first and second catheters being movable relative to each other.

21. The system of claim 20, further comprising the treatment material, wherein the treatment material comprises a medical adhesive.

22. A method comprising:
- introducing a vessel closure device into a vessel of a patient through a catheter lumen of a catheter, the vessel closure device comprising:
  - an elongated flexible member; and
  - a plurality of anchors attached to the elongated flexible member, the anchors of the plurality of anchors being distributed along a length of the elongated flexible member, wherein each anchor is fixably attached to the elongated flexible member to maintain a pre-determined interval from an adjacent anchor, and wherein each anchor comprises an anchor head configured to be introduced into a wall of the vessel and engage with the wall of the vessel to cause the wall to move in response to a proximal pulling force applied to the elongated flexible member;
- introducing the anchor head of at least one of the anchors of the plurality of anchors into the wall of the vessel; and
- after introducing the anchor head into the wall of the vessel, pulling the elongated flexible member proximally to cause the wall of the vessel to move radially inward.

23. The method of claim 22, wherein introducing the anchor head into the wall of the vessel comprises introducing the anchor head into the wall of the vessel such that the anchor head is at least partially embedded in the wall of the vessel.

24. The method of claim 22, wherein introducing the anchor head into the wall of the vessel comprises introducing the anchor head into the wall of the vessel at a treatment site, the method further comprising delivering a treatment material comprising a medical adhesive to the vessel at a position adjacent the treatment site.

25. The method of claim 22, wherein introducing the anchor head into the wall of the vessel comprises introducing a first anchor head into the wall of the vessel at a first treatment site, the method further comprising:
- after pulling the elongated flexible member proximally to cause the wall of the vessel to move radially inward, introducing a second anchor head of another anchor of the plurality of anchors into the wall of the vessel at a second treatment site; and
- after introducing the second anchor head into the wall of the vessel at the second treatment site, pulling the elongated flexible member proximally to cause the wall of the vessel to move radially inward at the second treatment site.

* * * * *